(12) United States Patent
Coates

(10) Patent No.: US 7,907,282 B2
(45) Date of Patent: Mar. 15, 2011

(54) INTEGRATED SENSING MODULE FOR HANDHELD SPECTRAL MEASUREMENTS

(75) Inventor: John Coates, Newtown, CT (US)

(73) Assignee: Microptix Technologies, LLC, Wilton, ME (US)

( * ) Notice: Subject to any disclaimer, the term of this patent is extended or adjusted under 35 U.S.C. 154(b) by 0 days.

(21) Appl. No.: 12/136,219

(22) Filed: Jun. 10, 2008

(65) Prior Publication Data

US 2008/0265146 A1 Oct. 30, 2008

Related U.S. Application Data

(60) Division of application No. 11/605,869, filed on Nov. 29, 2006, now Pat. No. 7,459,713, which is a continuation-in-part of application No. 11/355,908, filed on Feb. 16, 2006, now abandoned, which is a continuation-in-part of application No. 10/913,819, filed on Aug. 6, 2004, now Pat. No. 7,057,156.

(60) Provisional application No. 60/494,977, filed on Aug. 14, 2003, provisional application No. 60/740,850, filed on Nov. 30, 2005.

(51) Int. Cl.
*G01J 3/51* (2006.01)
(52) U.S. Cl. ........................................ 356/419; 250/226
(58) Field of Classification Search ............... 356/51, 356/419
See application file for complete search history.

(56) References Cited

U.S. PATENT DOCUMENTS

| | | |
|---|---|---|
| 2,649,011 A | 8/1953 | Black |
| 3,364,812 A | 1/1968 | Ewing |
| 3,370,502 A | 2/1968 | Wilks, Jr. |
| 3,460,893 A | 8/1969 | Wilks, Jr. |
| 3,508,830 A | 4/1970 | Hopkins et al. |
| 3,578,865 A | 5/1971 | Traver |
| 3,619,072 A | 11/1971 | O'Hara et al. |

(Continued)

FOREIGN PATENT DOCUMENTS

EP 0206433 12/1986

(Continued)

OTHER PUBLICATIONS

A.M. Toms, Preliminary Report on the Evaluation of FTIR for Lubricant Condit and Contamination determination in Support of Machinary Condition Monitoring. I. Synthetic Lubricants, Joint Oil Analysis Program (approx 1999).

(Continued)

*Primary Examiner* — Fannie L. Evans
(74) *Attorney, Agent, or Firm* — Dennis R. Haszko

(57) ABSTRACT

An integrated spectral sensing engine featuring energy sources and detectors within a single package includes sample interfacing optics and acquisition and processing electronics. The miniaturized sensor is optimized for specific laboratory and field-based measurements by integration into a handheld format. Design and fabrication components support high volume manufacturing. Spectral selectivity is provided by either continuous variable optical filters or filter matrix devices. The sensor's response covers the range from 200 nm to 25 µm based on various solid-state detectors. The wavelength range can be extended by the use of filter-matrix devices. Measurement modes include transmittance/absorbance, turbidity (light scattering) and fluorescence (emission). On board data processing includes raw data acquisition, data massaging and the output of computed results. Sensor applications include water and environmental, food and beverage, chemical and petroleum, and medical analyses. These can be expanded into various field and consumer-based applications.

22 Claims, 15 Drawing Sheets

Example embodiment of a spectral sensing engine:
integrated source, sample interface, spectral analyzer and detector

U.S. PATENT DOCUMENTS

| | | | |
|---|---|---|---|
| 3,665,201 A | | 5/1972 | Shea et al. |
| 3,713,743 A | | 1/1973 | Simms |
| 3,714,444 A | | 1/1973 | Carr et al. |
| 3,734,629 A | | 5/1973 | Griffiths et al. |
| 3,790,279 A | | 2/1974 | Skala |
| 3,876,307 A | | 4/1975 | Skala |
| 3,892,485 A | | 7/1975 | Merritt et al. |
| 4,054,389 A | * | 10/1977 | Owen ............... 356/419 |
| 4,365,303 A | | 12/1982 | Hannah et al. |
| 4,441,971 A | | 4/1984 | Ishiguro et al. |
| 4,570,069 A | | 2/1986 | Gager |
| 4,595,833 A | | 6/1986 | Sting |
| 4,649,711 A | | 3/1987 | Sibley et al. |
| 4,699,509 A | | 10/1987 | Kamiya et al. |
| 4,701,838 A | | 10/1987 | Swinkels et al. |
| 4,957,371 A | * | 9/1990 | Pellicori et al. ............... 356/419 |
| 4,975,581 A | | 12/1990 | Robinson et al. |
| 5,000,569 A | | 3/1991 | Nylund |
| 5,021,665 A | | 6/1991 | Ames |
| 5,049,742 A | | 9/1991 | Hosonuma et al. |
| 5,050,946 A | | 9/1991 | Hathaway et al. |
| 5,051,551 A | | 9/1991 | Doyle |
| 5,071,527 A | | 12/1991 | Kauffman |
| 5,076,397 A | | 12/1991 | Yamada |
| 5,077,477 A | | 12/1991 | Stroman et al. |
| 5,089,780 A | | 2/1992 | Megerle |
| 5,125,742 A | | 6/1992 | Wilks, Jr. |
| 5,166,755 A | * | 11/1992 | Gat ............... 356/419 |
| 5,185,640 A | | 2/1993 | Wilks, Jr. et al. |
| 5,196,898 A | | 3/1993 | Tamura et al. |
| 5,278,426 A | | 1/1994 | Barbier |
| 5,296,843 A | | 3/1994 | Wohlstein et al. |
| 5,319,437 A | * | 6/1994 | Van Aken et al. ............ 356/326 |
| 5,407,830 A | | 4/1995 | Altman et al. |
| 5,438,420 A | | 8/1995 | Harwick et al. |
| 5,440,126 A | | 8/1995 | Kemsley |
| 5,442,435 A | | 8/1995 | Cooper et al. |
| 5,452,083 A | | 9/1995 | Wilks, Jr. |
| 5,512,757 A | | 4/1996 | Cederstrand et al. |
| 5,534,708 A | | 7/1996 | Ellinger et al. |
| 5,548,393 A | | 8/1996 | Nozawa et al. |
| 5,568,186 A | | 10/1996 | Althouse |
| 5,608,518 A | | 3/1997 | Wilks, Jr. |
| 5,691,701 A | | 11/1997 | Wohlstein et al. |
| 5,739,916 A | | 4/1998 | Englehaupt |
| 5,741,961 A | | 4/1998 | Martin et al. |
| 5,790,246 A | | 8/1998 | Kuhnell et al. |
| 5,798,452 A | | 8/1998 | Martin et al. |
| 5,889,683 A | | 3/1999 | Ismail et al. |
| 5,939,727 A | | 8/1999 | Sommer |
| 6,040,578 A | | 3/2000 | Malin et al. |
| 6,043,505 A | | 3/2000 | Ames et al. |
| 6,049,088 A | | 4/2000 | Harding |
| 6,057,925 A | * | 5/2000 | Anthon ............... 356/419 |
| 6,091,484 A | | 7/2000 | Venica et al. |
| 6,094,604 A | | 7/2000 | Bucher et al. |
| 6,118,520 A | | 9/2000 | Harner |
| 6,138,082 A | | 10/2000 | Wang et al. |
| 6,151,108 A | | 11/2000 | Kwon et al. |
| 6,324,418 B1 | | 11/2001 | Crowley et al. |
| 6,331,704 B1 | | 12/2001 | Owen |
| 6,373,574 B1 | * | 4/2002 | Gu et al. ............... 356/419 |
| 6,383,209 B1 | | 5/2002 | Crowley |
| 6,388,251 B1 | | 5/2002 | Papanyan |
| 6,420,708 B2 | | 7/2002 | Wilks, Jr. et al. |
| 6,452,179 B1 | | 9/2002 | Coates et al. |
| 6,455,850 B1 | | 9/2002 | Coates et al. |
| 6,501,547 B1 | * | 12/2002 | Spencer et al. ............... 356/328 |
| 6,559,941 B1 | | 5/2003 | Hammer |
| 6,630,999 B2 | * | 10/2003 | Shroder ............... 356/419 |
| 6,690,452 B2 | | 2/2004 | Wilks, Jr. |
| 6,707,043 B2 | | 3/2004 | Coates et al. |
| 6,872,947 B1 | | 3/2005 | Greywall |
| 7,248,297 B2 | | 7/2007 | Catrysse et al. |
| 7,339,657 B2 | | 3/2008 | Coates |
| 7,660,678 B2 | | 2/2010 | Odegard et al. |
| 2002/0069021 A1 | | 6/2002 | Takezawa et al. |
| 2002/0185604 A1 | | 12/2002 | Coates et al. |
| 2003/0103150 A1 | | 6/2003 | Catrysse et al. |
| 2003/0154044 A1 | | 8/2003 | Lundstedt et al. |
| 2004/0201835 A1 | | 10/2004 | Coates et al. |
| 2005/0088653 A1 | | 4/2005 | Coates et al. |
| 2006/0284058 A1 | | 12/2006 | Coates et al. |
| 2007/0239367 A1 | | 10/2007 | Odegard et al. |
| 2010/0123897 A1 | | 5/2010 | Yang et al. |
| 2010/0134794 A1 | | 6/2010 | Odegard et al. |

FOREIGN PATENT DOCUMENTS

| | | |
|---|---|---|
| EP | 0797091 | 9/1997 |
| EP | 0836092 | 4/1998 |
| EP | 1077284 A2 | 2/2001 |
| EP | 1236807 A2 | 9/2002 |
| GB | 2346691 | 8/2000 |
| JP | 57142546 | 9/1982 |
| JP | 60111946 | 6/1985 |
| JP | 61213749 | 9/1986 |
| JP | 63266342 | 11/1988 |
| JP | 02259548 | 10/1990 |
| JP | 03111741 | 5/1991 |
| JP | 3142349 | 6/1991 |
| JP | 07280720 | 10/1995 |
| JP | 08062207 | 3/1996 |
| JP | 08201278 | 8/1996 |
| KR | 0150054 | 5/1996 |
| WO | WO8802109 | 3/1988 |
| WO | 2010/053617 A2 | 5/2010 |

OTHER PUBLICATIONS

Coates et al., A Rapid Field-Based method for the Determination of Soot in Used Diesel Oils, P/PM Technology, Dec. 1996, pp. 30-34, vol. 9, No. 6.

D.L. Wooton, Applications of Spectroscopy in the Fuels and Lubrication Industry, Applied Spectroscopy Review, (2001) pp. 315-332, vol. 36, No. 4.

LEM® Safeguards Against Diesel Fuel, Analyst, Inc., (1995) to 2000 and Oct. 2002) 4 pages total.

Standard Practice for Condition Monitoring of Used Lubricant Using Fourier Transform Infrared (FT-IR) Spectrometry, ASTM Draft Method (Oct. 4, 2002).

Coates et al., The Analytical and Statistical Evaluation of Infrared Spectroscopic Data from Used Diesel Lubricants, SAE Technical Paper Series, Fuels and Lubricants Meeting and Exposition, Oct. 1984, pp. 81-98.

EP 04809542.6, Supplementary European Search Report, 3 pages, Apr. 7, 2010, European Patent Office.

EP 04809542.6-2204, European Office Action, 7 pages, dated Jul. 14, 2010.

* cited by examiner

Example combinations of optical filters and detector components used for spectral sensing Figure 2A: Direct Coupling of Optical Filters and the Detector Array (LVF Version Illustrated)

Figure 2B: Example Integrated Detector Array Component With Filter Matrix

Figure 2C: Example Integrated Detector Array Component Mounted on Flex Connector Example embodiments of the spectral engine with sample interface tips Spectral Sensor with Pipette-style Tip Spectral Sensor with Alternative Flow or Dip Tip Common Spectral Engine

INTEGRATED SENSING MODULE FOR HANDHELD SPECTRAL MEASUREMENTS

CROSS REFERENCE TO RELATED APPLICATIONS

This application is a divisional application of co-pending application Ser. No. 11/605,869, filed on Nov. 29, 2006, which is a continuation-in-part of application Ser. No. 11/355,908, filed on Feb. 16, 2006, (now abandoned) which is a continuation-in-part of application Ser. No. 10/913,819, filed on Aug. 6, 2004 (now U.S. Pat. No. 7,057,156), which in turn claims priority under 35 U.S.C. §119(e) from provisional patent application Ser. No. 60/494,977, filed on Aug. 14, 2003. This application also claims priority under 35 U.S.C. §119(e) from provisional patent application 60/740,850 filed on Nov. 30, 2005.

FIELD OF THE INVENTION

The present invention relates to a miniaturized integrated spectral sensor, with integrated sensed signal conditioning, signal exchange, and integration into a handheld device for the measurement of solution and solvent-based chemistries. With adaptation, the device can be configured for solids or gases, but liquids are the preferred implementation. The sensed information is converted into meaningful information in the form of concentrations of specified species and for the composition or properties of mixtures and composite materials.

BACKGROUND OF THE INVENTION

In a traditional laboratory, instruments described as spectrometers, spectrophotometers or photometers (referred to from here on as spectrometers) are used to make measurements on liquids or solutions containing one or more chemical substances. Such methods of analysis are used to measure the concentration of a component either directly or following the reaction with one or more chemical substances, usually described as reagents. In such reactions the analyte, or material being measured, is converted into a chemical form that can be detected within the spectral region covered by the instrument. Examples can include the formation of a specific color, or the formation of a material that provides a characteristic fluorescence or luminescence, especially in the presence of radiation of specific wavelengths, such as an ultraviolet source, or the formation of a light scattering medium, where the degree of light scatter is proportional to the concentration of the analyte (substance or species being measured). This latter case includes turbidity for the measurement of suspended materials. In certain spectral regions, such as the ultraviolet, near infrared and the mid infrared, materials can have natural absorption characteristics, where the material can be measured directly in the absence of a reagent. Similar situations occur where an analyte is naturally colored or naturally fluorescent. In these situations reagents are not required.

The normal procedure in a laboratory is to prepare the sample for analysis. The circumstances described in the preceding paragraph above are for the measurement of samples in a liquid form. Spectral measurements are not limited to liquids, and samples that exist as solids or gases can be considered for spectroscopic analysis if prepared in a form that can be measured. For most applications involving reagents, a liquid-based medium is implied. Both solids and gases can be handled if dissolved within a reagent system, or if dissolved in a suitable solvent. If the sample has its own natural spectral response, in the absence of a reagent, the sample may be studied in its natural form as a solid or gas. Such measurements require some form of specialized sample handling accessory. Samples existing in the liquid state are often preferred for reasons of convenience of sampling and handling, and because the sample as studied is generally homogenous and representative of the whole sample.

The standard approach to handling liquids is to place the sample with a container with optically transparent walls or windows. Such containers are called a cells or cuvettes (referred to from here on as cells). If the sample must be treated with a reagent prior to analysis then the sample is normally placed in a separate container, such as a laboratory flask or bottle, prior to placement within the cell. Such a preparation can also require heating or an incubation period. Once the sample is transferred into the measurement cell, the cell is placed at a sampling point within the spectrometer. Typically, this sampling point is a chamber or sampling compartment, which is often light-tight, and can be sealed from interference from ambient light. The sampling chamber may be configured to accept one or more sampling cells. In an alternative rendering, the sample cell may be configured for sample flow through the cell. In such systems, a reagent may be introduced in the sample flow, enabling the regent to interact with the sample in situ.

Most laboratory instruments occupy bench space, and as such they can be limited in terms of access. Furthermore, most laboratory instruments are relatively expensive, and so the number of instruments available for use by laboratory personnel may be limited. In recent years, smaller and lower cost instruments have become available, but these can cost several thousands of dollars once they are configured to be a fully functional instrument. Many of the newer generation of instruments utilize fiber optic cables to couple the spectrometer to the sample. While these present some flexibility, they are also constrained by the length of the fibers and the overall lack of flexibility of the cable. All cables and fibers are limited in their flexibility by their bend radius. Also, fiber optics can impose signal quality issues on the collected spectral data that can negatively impact the final results unless careful consideration is given to the way the system is implemented.

In certain industries and for certain applications, such as environmental measurements, it is desirable to make measurements in a non-laboratory environment. Examples can include measurements on water samples taken at an industrial site or from a stream, river or lake for contaminants or undesirable materials. In such cases, the measurements ideally must be made on a portable instrument. In the absence of a portable instrument there is the burden of sending collected samples back to a laboratory for analysis. Most portable instruments still require the use of a cell, and most require samples to be prepared by mixing with reagents followed by a transfer to the cell. This is not always a convenient scenario. The ideal situation would be to sample directly after the reagent is added without the need to transfer to a cell, or if possible to sample directly from the source, where the reagent is introduced as part of the sample handling. Such systems are not currently available for field-based (non-laboratory) sample handling. Thus, while small format instruments exist and are used for standard types of measurements with standard cells, they still possess many of the limitations of traditional instruments. Also, it is normal for most portable instruments to be restricted in performance and perform a small number of fixed analyses.

SUMMARY OF THE INVENTION

The present invention uses a miniaturized, low cost spectral sensing device, a major advancement in measurement opportunity over the status quo, and overcomes issues related to size or space occupied in the laboratory, or the size of a portable spectrometer. Each device is intended to provide the functionality of a normal spectrometer or spectral analyzer, but at reduced cost, and with a significantly reduced size for the total package.

The spectral sensing component of the present invention is based on existing optical sensing technology constructed in accordance with the principles set forth in commonly-owned U.S. patent application Ser. No. 10/913,819 filed Aug. 6, 2004 (now U.S. Pat. No. 7,057,156), incorporated herein by reference, in its entirety. The spectral sensing systems described feature specially assembled detection devices that incorporated the spectral selection elements required to generate the spectroscopic data for subsequent analysis. One set of examples are linear variable filter (LVF) systems based on a silicon photodiode array that can offer spectral ranges of 360 nm to 700 nm (visible) and 600 nm to 1100 nm (short wave near Infrared (NIR)). This also includes multi-element detectors that feature filter mosaics or filter arrays, such as multi-element color sensing devices. The current implementations feature the spectral selection devices, nominally in the form of interference filters (LVF or otherwise) that are produced as an integrated component as part of the detector array fabrication, either by the array manufacturer or by a company specializing in thin film deposition.

In likeness to the patent application referenced in the preceding paragraph, the current invention includes full integration of the sample handling with the spectral sensing, and the spectral measurement electronics. The sample interface, the light source for the spectral measurement, the spectral detection system, the primary signal acquisition electronics, and the signal processing and display of the final analytical results are provided within a single package. In one of the proposed forms, the package includes a sample transport mechanism whereby the sample, in liquid form, is drawn into the measurement area by an integrated pumping or suction device. Said pump is either mechanically actuated by a spring or suction mechanism or electrically actuated by a suitable micro pump. The sample area is integrated within a disposable sampler, and can be similar in concept to disposable pipettes or to the disposable tips used for micro-pipette systems. In one form of the samplers, denoted as Smart Tips™ or Smart Samplers™, the reagents are included in an immobilized form. When these samplers are used, the sampler is constructed to provide mixing of the reagents either prior to entry into the measurement zone, or within the measurement zone, thereby eliminating the need for external handling or mixing of reagents. An option is included to make these Smart devices identifiable to the measurement system either by mechanical (keyed) or electronic means. The spectral sensing systems can take a form similar in size and construction to a single-channel micro-pipette or a general purpose dispensing system, and can be battery powered. The systems can include hardwired communications to a PC, laptop or handheld PDA via standard interfaces, such as USB, and can have the option for wireless communications via one of more of the standard protocols such as BlueTooth, ZigBee, IEEE 802.11b/g or equivalent standards.

It is an object of the present invention to provide an integrated spectral sensor. The term integrated is used to indicate that the device is to be fabricated as a single structure, where the components are intimately interconnected in a miniaturized platform. The system includes a sampling component, a spectral engine including a light or energy source and a sensing component and a signal conditioner, a signal exchange system, and a controller, all assembled as a single interconnected structure. The interfacing optics form part of the structure, with no requirement for additional imaging elements such as lenses or mirrors, as used in spectrometers, and as such is differentiated from traditional instruments and spectrometers. The system can be configured to measure light/energy absorption or light/energy emission (as in fluorescence or luminescence). In the standard form the sampling component is in the form of a separable chamber with tip and optional sample transport mechanism (alternative designs can feature a separated pumping device), which can be made of a suitable material, such as a common plastic, that renders the part disposable. The sampling component interfaces intimately with the spectral engine that includes an optical sensing system for nonintrusive detection of the spectral or optical characteristics of the sampled medium (normally a fluid). The spectral engine further includes a light or energy source, spectral sensing component, featuring a fully integrated spectrally selective detection device (described as a spectrometer or a photometer on a chip or alternatively as an integrated sensing module including integrated circuit components), for measuring the characteristic chemical or physical features of the sample medium, an interface for a removable sample cell or chamber that is intimately connected to the source and sensing element, and is dimensionally optimized and matched to these components, and a microprocessor for conditioning the signals output from the spectral sensing element. Additional functions of the microprocessor include spectral data extraction, and the calculation of chemical composition or properties, method and calibration storage, and data communications. The signal exchange system may be a wired or a wireless signal transfer device coupled locally or remotely to the sensor. The primary power for the electronics is provided nominally via batteries, which can be of the rechargeable variety if required. However, the option to use tethered power, such as via a USB cable is included.

In its standard format the spectral sensing device includes an integrated sample transport system to provide a means to introduce the sample fluid into the measurement region. In its simplest form, this sample transport is provided via a simple squeeze bulb, suction bellows or spring-driven piston pump, as implemented in commercial micro-pipettes. In an optional form, a piston device or another form of pump, such as a piezo-driven micro-pump, features an electronically controlled drive mechanism. Swept sample volumes can be small, being of the order of a few hundred microliters to a few milliliters (dependent on pathlength), at the most, and so the pumping capacity can be correspondingly low.

In its standard form the fluid is drawn into the measurement region of the sensing device, as noted, via an integrated pump or suction device. The measurement region is a removable component, defined as a sampler, and is implemented in the form of a modified pipette-like structure, where the fluid is drawn in through a tip. The sampler measurement chamber includes reflective elements encapsulated and/or retained within the construction. These reflective elements capture the light/energy emerging from the source mounted within the optical interface of the spectral engine. This light/energy is then returned, in a retro-reflective manner back to the spectral sensing element (detector), which is also mounted within the optical interface of the spectral engine. In this mode of operation, the light/energy passes through the fluid at least three times; twice to and from the spectral engine and once between the two reflective elements. This produces a composite dimension, which is known as the pathlength. This is equivalent to a single pass through a conventional liquid cell. These dimensions can be set to be equivalent to normal pathlengths used in conventional cells, and these will be nominally from 1.0 mm to 10.0 cm (total distance). It is expected that in the standard format, this measurement chamber will be constructed from an optically transparent medium, and for most applications, this will be a clear plastic material. The latter is to be constructed as a molded part in the most common implementation of the device. The total sampler construction can be produced in two or more parts, with the inner measurement area being encased within a black and/or optically opaque external shell. In the common implementation this can be made as a co-extruded part, or as an assembly made from two or more separate molded parts. Note that the optically opaque exterior of the sampler will make a positive light seal with the outer casing of the main measurement system. In this manner, the measurement area is shielded from external light sources, thereby ensuring accurate photometry, and also enabling low-light measurements, such as fluorescence and luminescence.

In the standard mode of operation it is assumed that the fluid being measured will already contain an active chromophore (light absorbing entity related to the analyte) or fluorophore (light emitting entity related to the analyte). This chromophore/fluorophore will either be native to the material being measured or induced by the use of one or more specific reagents. The mixing of reagents to form a measurable solution is a standard practice in most testing laboratories, and it is also a standard procedure for most field-based testing. The micro-spectral sensing system described in this package has the advantage that the swept volume required for the fluid by the measurement system is in the region of a few hundred microliters to a few milliliters. This reduces significantly the overhead for reagents, and it also reduces the environmental impact for disposal of the fluid after analysis. This provides an additional advantage insofar as it makes some measurements practical that would be otherwise too expensive to perform because of the high intrinsic cost of the reagent. Examples of such measurements exist in the biotechnology and medical testing areas.

In an attempt to make the interaction of reagents with the fluid under study more efficient, in terms of ease-of-use, removing the need for mixing vessels, reducing exposure to reagents, and significant cost reductions for expensive reagents, Smart Tips™ or Smart Samplers™ are used. Smart Tips/Samplers are designed to enable reagent interaction and mixing to be carried out in situ, without the need for external reagents or mixing vessels. The internal architecture of the tip or sampler includes molded features that generate turbulences when the fluid is drawn into the tip. Just sufficient reagent (or reagents) to fulfill the requirement of the analysis can be located in an immobilized form (encapsulated in a water/solvent soluble solid medium or a hydrophilic medium) adjacent to the entrance of the tip. The medium and the reagent can dissolve in the sample or interact with the sample as it enters the tip or sampler, and the consequent solution can be agitated during its passage into the measurement region. An option in the design is to key the fitting of the tip to the body of the measurement system in a way that the specific analysis can be automatically defined within the measurement device. This can be accomplished either by a physical key, or via electronic means, such as a bar code, a digital bar code, or by a technology such as RFID. In the case of the digital bar coding, this can be implemented by the use of an additional, well-defined chromophore/fluorophore (non-interfering) mixed in with the reagent.

As indicated, the spectral measurement device is primarily intended for use with fluids. However, optional tips/samplers and optional optical interface layouts will be considered for measurements of solids and gases. These optional tips/samplers may be simple adaptations of the existing tips/samplers, such as the combination of an embedded chromophore located within the optical path, where this chromophore interacts with a reactive component in a gas or vapor. In the case of solids, the analyses can be made by direct contact with the surface material based on a diffuse reflectance or interactance method of measurement.

Numerous application areas have been identified that can benefit from this integrated sensor approach, and these include the water quality measurements for environmental and public safety requirements, general laboratory testing for food, beverage and consumer products, applications in the chemical and petroleum industries, and medical and clinical applications. Most of these applications already have prescribed and developed methods, and where reagents are involved, the reagent chemistries are already standardized, and the materials are readily available, either as prepared chemicals or in kit form. Many of the methods are standardized by agencies such as the EPA, ASTM, the FDA, the USP, and the AOAC (food and beverages). The system described herein is a convenient, low cost and rapid system to enable these measurements in almost any work environment. As noted earlier, not all analyses require chemical reagents. Those materials containing natural chromophores/fluorophores can be measured directly, and as in the case of reagent-based chemistries, standardized methods for measurement and data presentation already exist. The applications go beyond those mentioned, including those linked to consumer products and consumer-important measurements. It is to be understood that the present invention has broader applicability than the application areas cited.

The standard methods of analysis that are referenced in the preceding paragraph normally involve some form of formula for the calculation of the final results. The formula often contains numerical relationships and coefficients that are applied to the raw data and these are determined by running predefined calibration standards. The system as described can be used to develop this type of calibration. The calibration can be carried out within a controlled environment, and with a live connection to a PC or laptop computer for data logging and storage. The calibration set can then be handled by an established procedure, such as a Beer-Lambert based calculation of light/energy absorption versus concentration relationship. The coefficient(s) and intercept can be downloaded into the measurement system along with measurement settings and criteria. Complex applications can require multivariate modeling, and in such cases the modeling equations can be downloaded. The architecture of the onboard microprocessor can be sufficiently flexible to accommodate such downloads, and can accommodate multiple models/calibrations, dependent on the size of the calibration data, and the available onboard memory storage. This enables an end-user to customize the measurement system for a broad range of applications. The system is not limited by design to fixed analyses. Individual methods stored in the measurement system can be recalled at anytime, by a user interface linked to the display on the front of the unit.

The method of uploading (results) and downloading (methods and calibrations) can be enabled via either direct physical coupling to a PC, laptop computer or handheld PDA, or via a wireless connection. Options for direct coupling can be via a standard serial interface, such as a USB port, or via some other standardized interface such as Ethernet or Firewire. The wireless connection can be optional, and can be implemented on board the main electronics in a standardized format, such as BlueTooth, ZigBee, or a standard IEEE 802.11b/g or IEEE 802.14b. In order to implement the Ethernet option, or the wireless option, the device can be provided with a user-configurable IP address. In this form, one option for communication with the device can be from a web server, which will provide the option for remote access for upload and download.

The integrated sample, sensing and data of the present invention provides a more efficient method of fluid sample analysis than conventional instruments. This and other advantages will become more apparent upon review of the following detailed description and the accompanying drawings.

DETAILED DESCRIPTION

Figure 1:
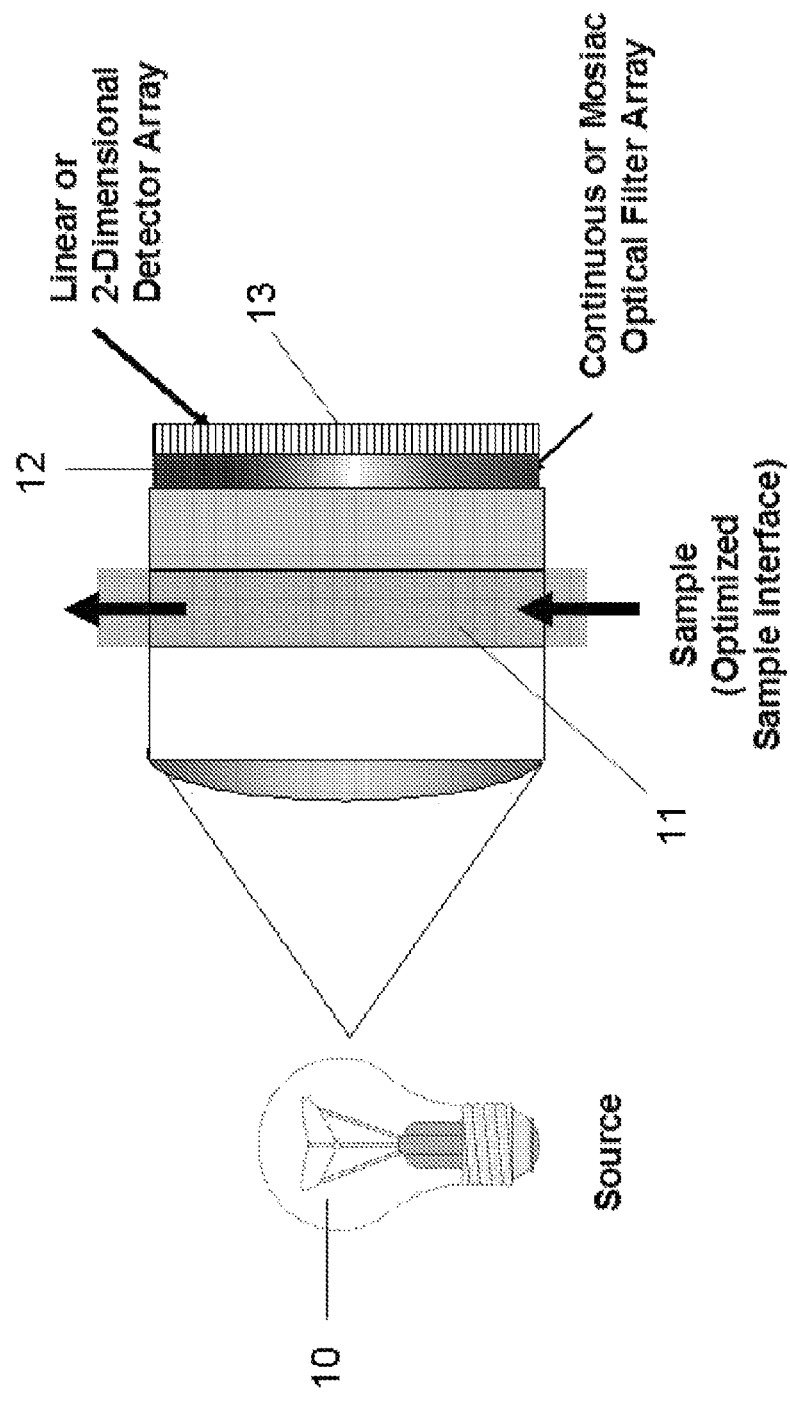
FIG. 1 is a cross section of an example embodiment of a spectral sensing engine: integrated source, sample interface, spectral analyzer and detector.

The present invention is an integrated handheld measurement system for spectral sensing of aqueous and organic solutions, certain gases and vapors, and for certain solid substrates, such as powders and extended solid surfaces. The sensing aspect of this invention preferably includes one or more miniaturized optical spectral sensors located within the body of the handheld device. Several different embodiments are described for the body of the device, and examples are cited later in FIGS. 6 to 13. FIG. 1 provides a symbolic representation of an example spectral sensing system, comprising a light or energy source 10, an optimized and integrated sample chamber 11, a spectral analyzer or spectrally selective element 12, and an integrated detection system 13. Example embodiments of such spectral sensing systems are illustrated in FIGS. 4 to 10. In the configuration shown in FIG. 1, the source is indicated as an incandescent-style of source, such as a tungsten source. The invention covers various types of sources, such as solid-state sources (LEDs and diode lasers), MEMs-based thermal sources and gas discharge devices, where the source is optimized for the application and the spectral range of the overall spectral measurement system. The optical layout shown in FIG. 1 represents an energy/light transmission (or absorption) style of measurement. The technology, enables light scattering and optical emission measurements, such as fluorescence, phosphorescence, and luminescence, and can also be configured for reflectance and transflectance (transmission-reflection) measurements from surfaces. The latter is indicated as an example embodiment in FIG. 8. The individual spectral sensors are intended to be small and convenient to use, and can be optionally fabricated as low cost devices. As such, multiple implementations of the handheld devices can exist in the work place, or even in the home. An optional component of the system is a wireless communications interface, based on a standard wireless platform, and conforming to published standards such as the IEEE 802.11b/g, ZigBee and Bluetooth. The system design includes the wireless components located on the main electronics board(s) as shown, for example, in FIGS. 4 and 5. The objective of the wireless components is to provide an easy mechanism to download results from the spectral measurement device, and to upload new calibrations and measurement schemes.

Figure 2:
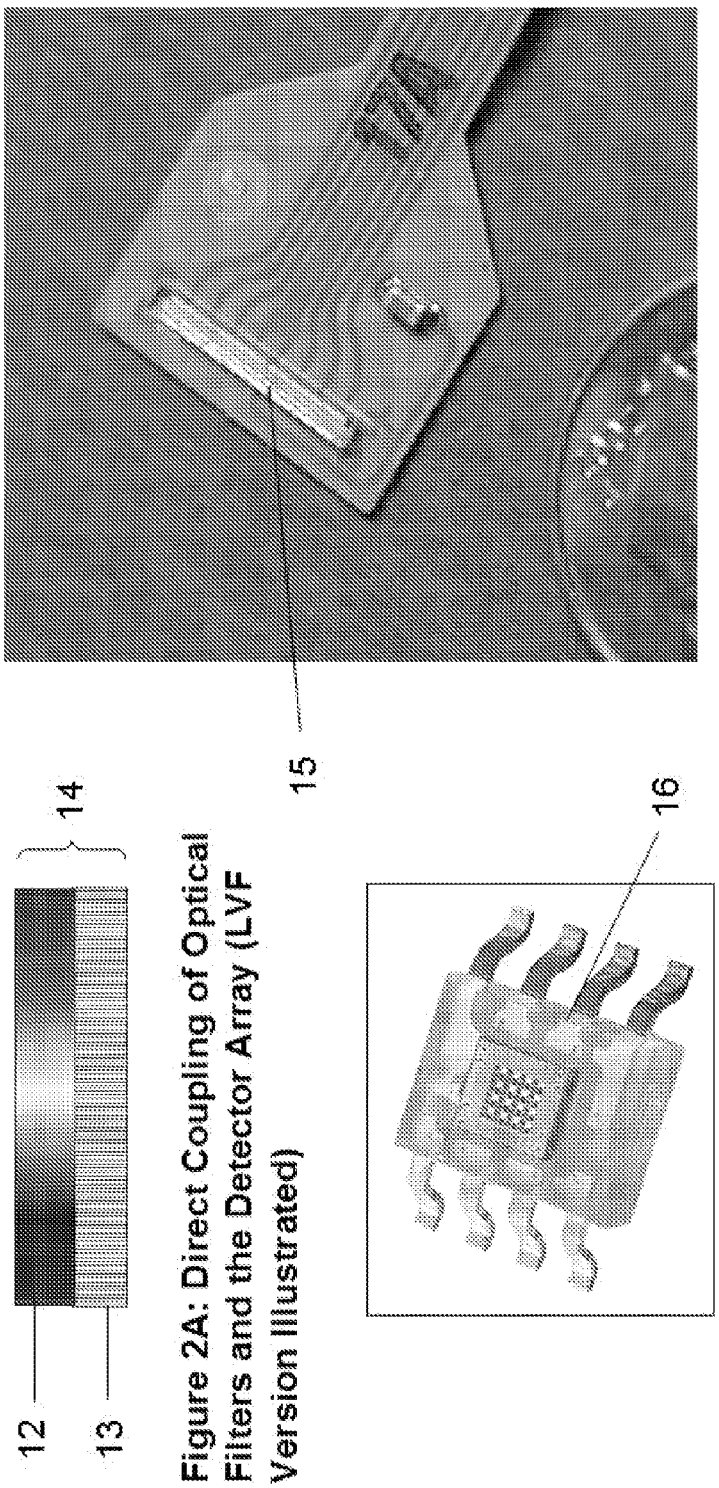
FIGS. 2A, 2B and 2C are example combinations of optical filters and detector components used for spectral sensing.
Figure 10:
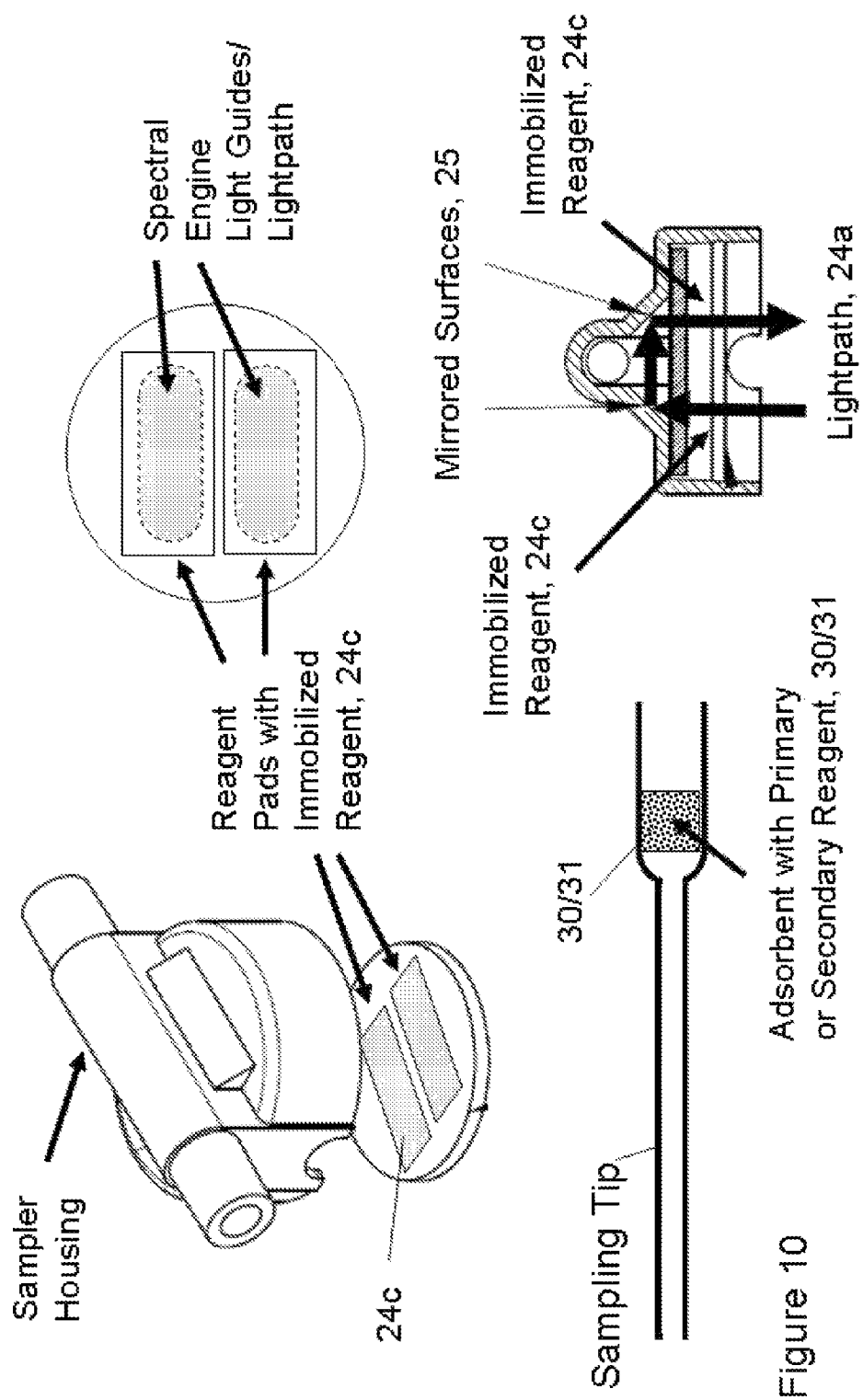
FIG. 10 illustrates an alternative embodiment showing the Smart Sampler™ with immobilized reagents in the tip or the sample housing.
Figure 14:
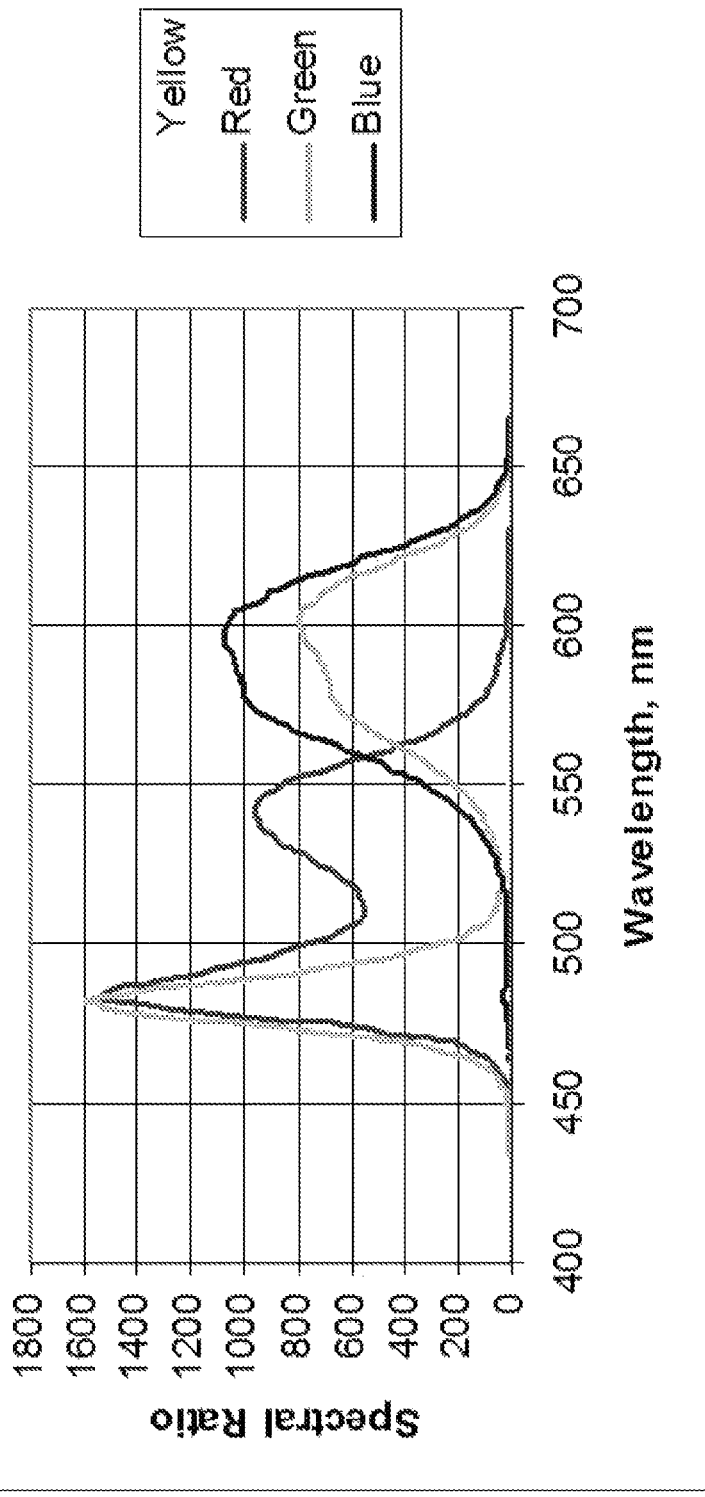
FIG. 14 illustrates an example spectral sensor response in the visible region: colored dye solutions.
Figure 15:
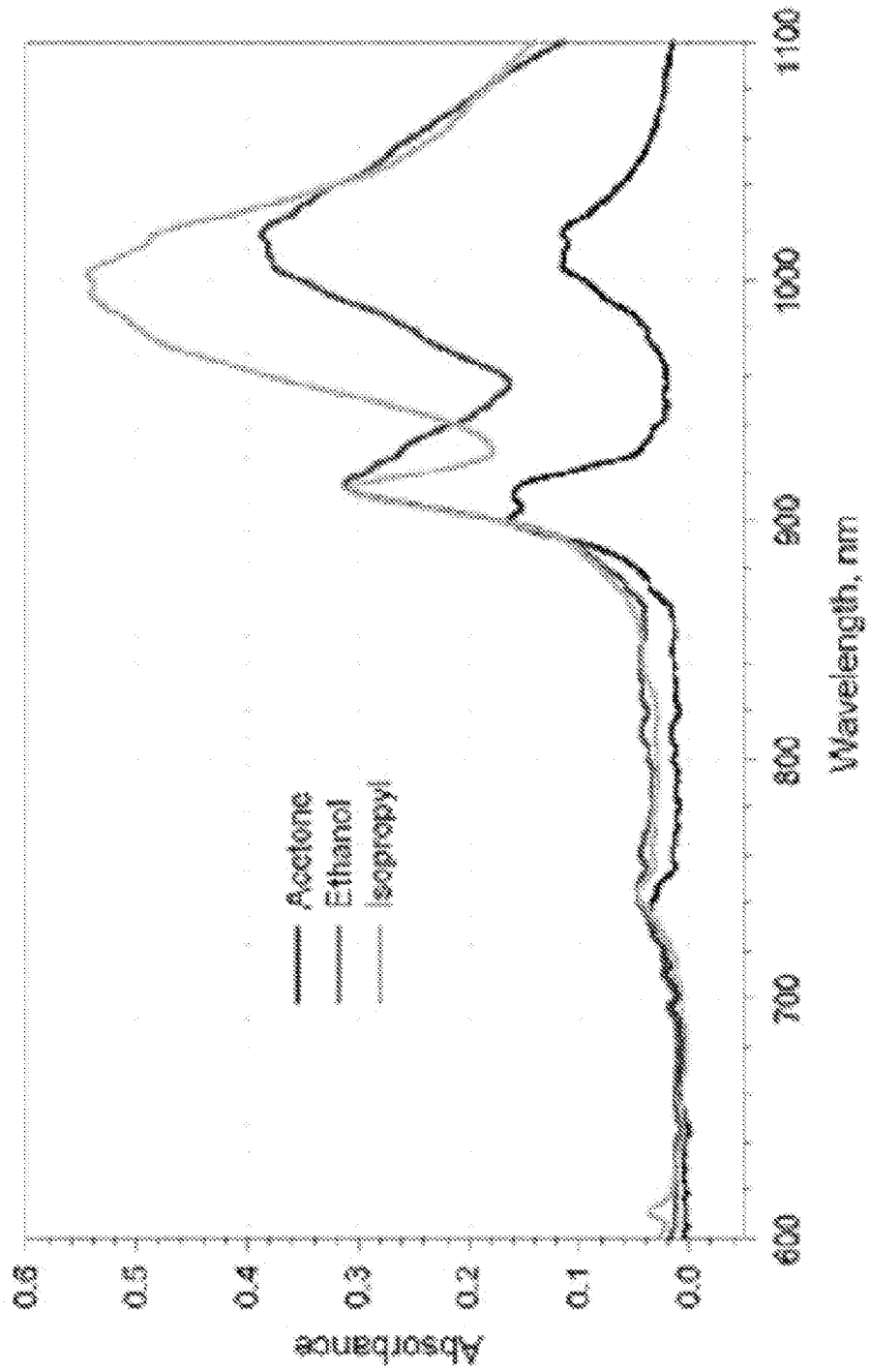
FIG. 15 illustrates an example spectral sensor response in the near infrared region spectra of common chemicals.

An important component of the spectral sensor technology can be broadly described as an optical spectrometer on a chip as represented in FIG. 2 by 14, 15 and 16. Such an optical spectrometer on a chip thus forms an integrated sensing module having a detector that includes a solid-state device either matched directly in spectral response to a source, or capable of responding to wavelengths over a broad spectral range from one or more sources, sensitive in spectral regions of UV (230 nm to 400 nm), UV-visible wavelengths (350 nm to 700 nm) near infrared (600 nm to 2500 nm) and mid-infrared (2.5 µm to 25 µm, 2500 nm to 25000 nm). While optical sensors have been available, the present invention integrates an optical filter assembly 12 with a light or energy sensitive array 13 (FIG. 1). The optical filter technology used is either in the form of a continuous linear variable filter (LVF) 14, 15, or a filter array (patterned filter or mosaic) 16. In the LVF form, the resultant device or spectral sensing component 14, 15, is the most versatile and can be utilized for many applications, and for different spectral ranges, dependent on the detector array technology used. An example format of an LVF-based spectral sensor is shown in FIGS. 1, 2A and 2C. In low-cost examples, the spectral sensing component is preferably implemented as part of a photodiode or a Complementary Metal-Oxide Semiconductor (CMOS) array detector package 15. In the current embodiment, the LVF is directly bonded to the detector array, which preserves the spectral resolution of the LVF. In this form the assembly does not require any form of resolution retaining optics. Sensors derived from these components based on the LVF can be used for absorption measurements in the mid-range UV, long-wave UV, the visible and the short-wave near infrared (NIR), as well as fluorescence measurements in the visible and NIR. Examples of data have been acquired in all of these modes, and example spectral response curves for the visible and NIR ranges are provided FIGS. 14 and 15, respectively. The short wave NIR provides good differentiation based on chemistry and composition based on vibrational overtones of the component molecules. This spectral region can be applied to organic and inorganic compounds, and also aqueous solutions containing high concentrations of solutes. However, in cases, such as the digestions in pulp and paper applications, where visible absorbing and fluorescence centers are also expected to be important, the visible version for the spectral sensor can also be used. For applications involving chemistry, where the species to be measured is not normally visible, the analysis may be performed with the addition of a reactive chemical reagent. For many applications, reagent-based chemistries are the basis for standard laboratory measurements, where the reagent and the sample are manually mixed prior to the analysis. The analysis typically involves a visible (color) or fluorescence based measurement. In an alternative configuration of the sample handling interface, for the handheld pipette-style of sensor (FIGS. 6 and 11) or the chamber-based handheld sensor (FIGS. 7 and 12), the reagent is immobilized within the tip of a Smart Tip™ (FIG. 9) or within the tip/chamber of a Smart Sampler™ (FIG. 10).

Figure 3:
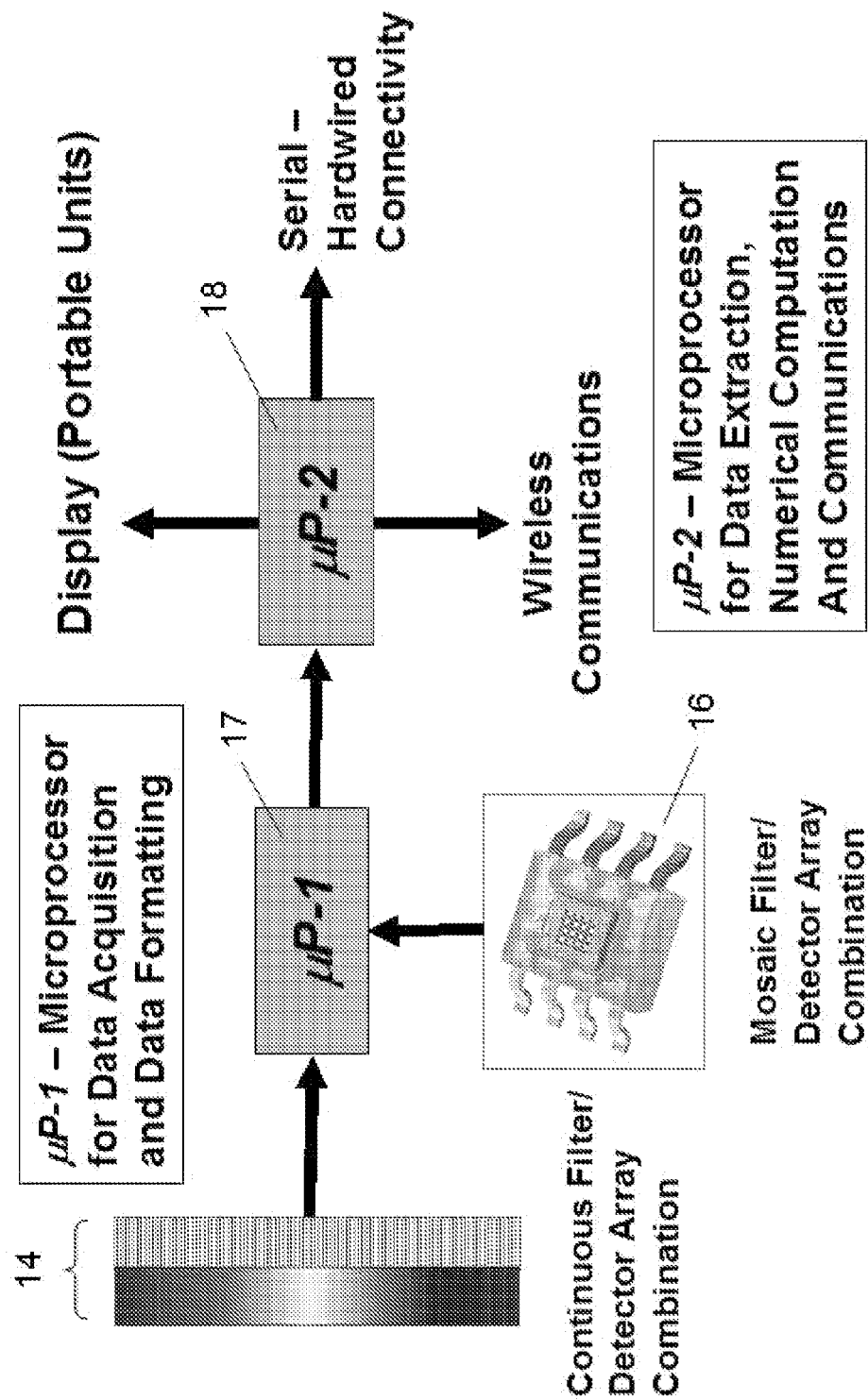
FIG. 3 illustrates example electronic components for the integrated spectral sensor.

As defined, the spectral sensor can be constructed from either a continuously variable filter (defined as the LVF) 14 or from a filter matrix or mosaic 15. This latter approach is usually optically more efficient and less expensive than the LVF approach. It is often more specific in application, but less versatile than the LVF system. An illustrated example of a matrix-based spectral sensor 16 is provided in FIGS. 2 and 3. The version shown is a 4-channel RGBW (Red-Green-Blue-White) sensing device, and is capable of handling a wide range of color-based applications. Custom versions of this sensor, featuring more than 4-optically selective channels can be used. New technologies, involving the deposition of the wavelength selective devices on the surface of the detector elements can be used to make application specific detection devices. In such cases, the mosaic can feature both the optical filter and the detector as discrete components. Such devices can be assembled as hybrids, providing spectral detection in more than one spectral region, such as a combination of the UV, visible and NIR. An example application can be for the measurement of bio-materials, such as proteins and amino acids, where one or more solid state excitation sources are used (such as 280 nm and 340 nm), and where detection is made in the UV (ca. 340 nm) and in the visible.

The sensor hardware for the present invention is not limited to silicon-based photo-sensing devices, and alternative detector arrays can be used, including InGaAs, PbS, PbSe, LiTaO$_4$ and also MEMS-based devices. Such devices would be considered for extensions into the longer wavelength NIR and for the mid-IR. The format of the proposed sensor platform may be extended into these other spectral regions. For these cases, alternative optically transparent media may be required for the sample chamber and the optical conduit construction, and these can include materials such as quartz, sapphire and zinc selenide.

The onboard electronics that form part of the spectral engine (FIGS. 3 to 5) provide for the primary data acquisition from the spectral sensing/detection devices. Initially, the raw signal obtained needs to be conditioned and scaled. This is effectively a transformation from the raw signals from the physical device to a spectral based data array (or spectrum), defined in wavelength (or energy) units (x-axis) and intensity units (y-axis). A standardized or unified data format (UDF) is used to provide a well-defined start and end to the spectral data, and with a clearly delineated data interval (data point spacing). The signal handling and these primary data transformations are shown as a symbolic representation in FIG. 3, and are handled by what is defined as µP-1 (microprocessor function 1) 17. In order to complete an analysis, it is usually necessary to extract the relevant intensity information from one or more predefined regions of a spectrum. This intensity data is further manipulated by one or more numerical functions, which normally include unique calibration data for the species being measured. These additional mathematical functions are performed by the symbolic representation defined as µp-2 (microprocessor function 2) 18 and these are incorporated in what is defined as a method. The methods, which are downloaded into the memory (such as flash RAM) or the system, include data acquisition instructions, spectral data pre-processing, data extraction from the spectra, and also the subsequent calculations to provide the final answers. Those skilled in the art of optical sensing technology will recognize that the short-wave Near Infrared (700 to 1100 nm) works well for a wide range of liquid-based measurements. Although spectral changes in this region are subtle, they can be readily correlated with both composition and key chemical and/or physical properties. Tools such as multivariate modeling, sometimes known as chemometrics are common for such applications. These are used, as appropriate, and the calibration coefficients generated from the modeling are stored on memory (such as flash RAM) associated with one or more microprocessors associated with µP-2, FIG. 3 (17 and 18), located on-board the sensor. Note that the functions for µP-1 and µP-2 can be combined in a single processor if required. The flash RAM can be either present as separate memory components, or integrated into the microprocessors. It is noted that this numerical treatment is not unique to the NIR spectral measurement range, and the onboard computing facilities defined will also be used for resolving complex mixtures in other spectral regions served by the handheld devices described in this invention. The component labeled µP-2 18 can also handle communications and display functions. Communications can be either hardwired, such as a standard serial COM device (UART function on mP-2) or as a USB device, or as wireless communications. The latter can be incorporated as components with separate functionality from µP-2 18. The display function can include an onboard display for the handheld sensor, and can range from a simple multi-line display to a full-scale RGB XGA or other standard display device.

Figure 4:
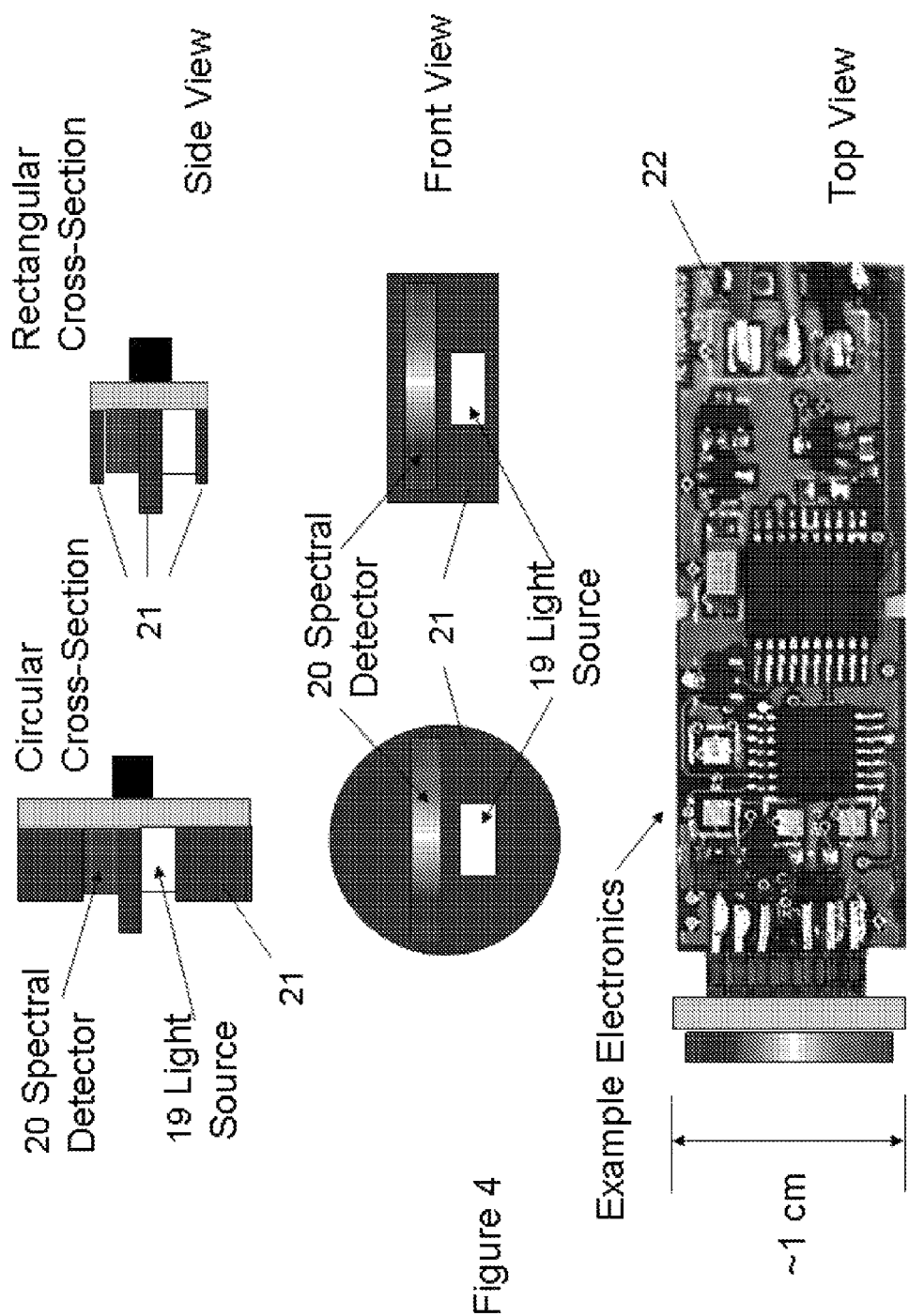
FIG. 4 illustrates example embodiments of the spectral sensing components-electronics.

In the practical implementation, the spectral sensing elements can be fully integrated as a single entity or assembly on what are described as the sensing components in FIG. 4. This optical sensor assembly (or opto-board) includes the light source 19 and the spectral sensing element or detector 20. These devices are optically isolated from each other by an optical mask fabricated from an optically opaque material 21, such as a carbon-filled elastomer. Example embodiments are shown in FIG. 4 with circular and rectangular cross-sections. The choice of cross-section is dependent on final sensor configuration and application. The main system electronics board 22 is directly coupled to the optical sensor assembly via either a hard connector on the back of the opto-board, or via internal cabling or flex-based connectors.

Figure 5:
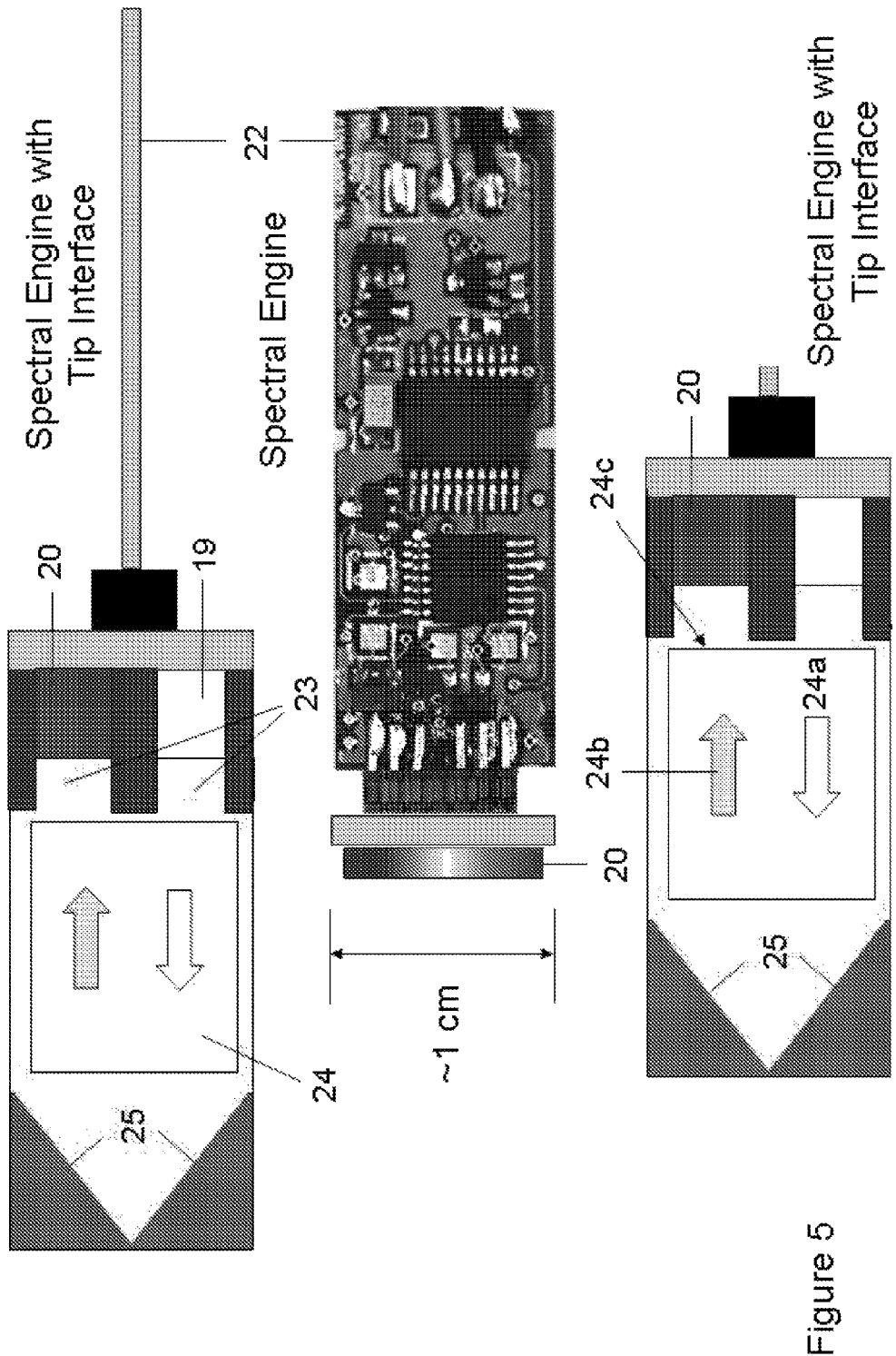
FIG. 5 illustrates an example embodiment of the spectral engine component-sample integration.
Figure 6:
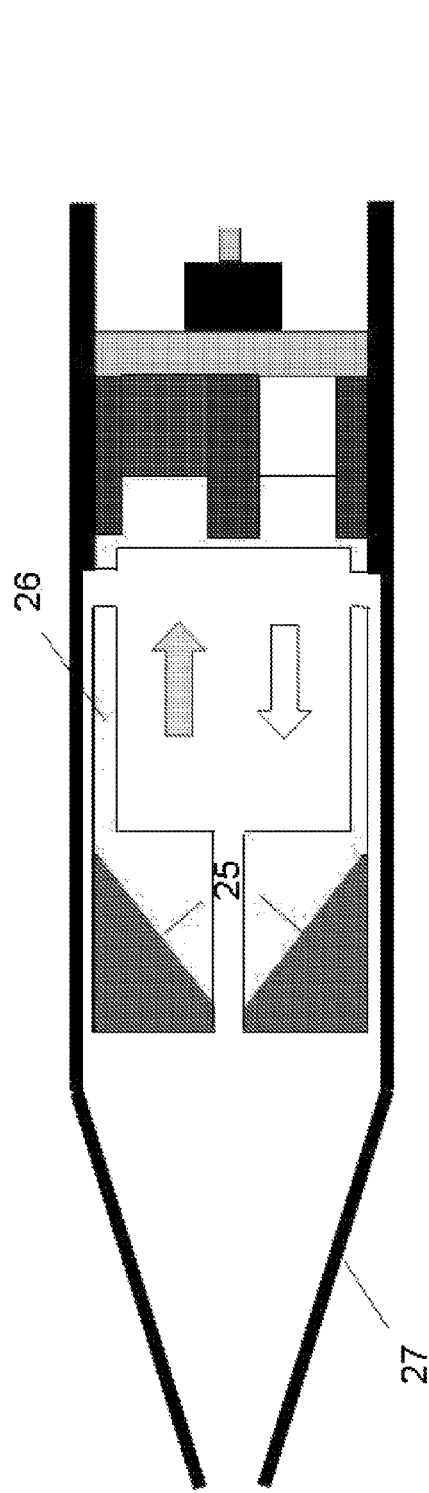
FIG. 6 illustrates example embodiments of the spectral engine with sample interface tips.
Figure 6:
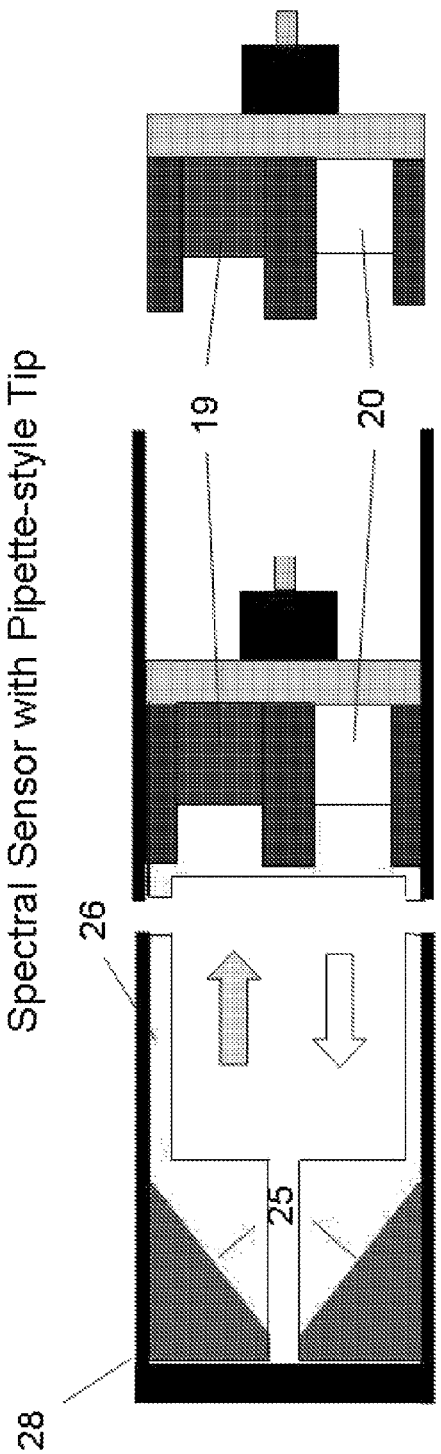
Figure 7:
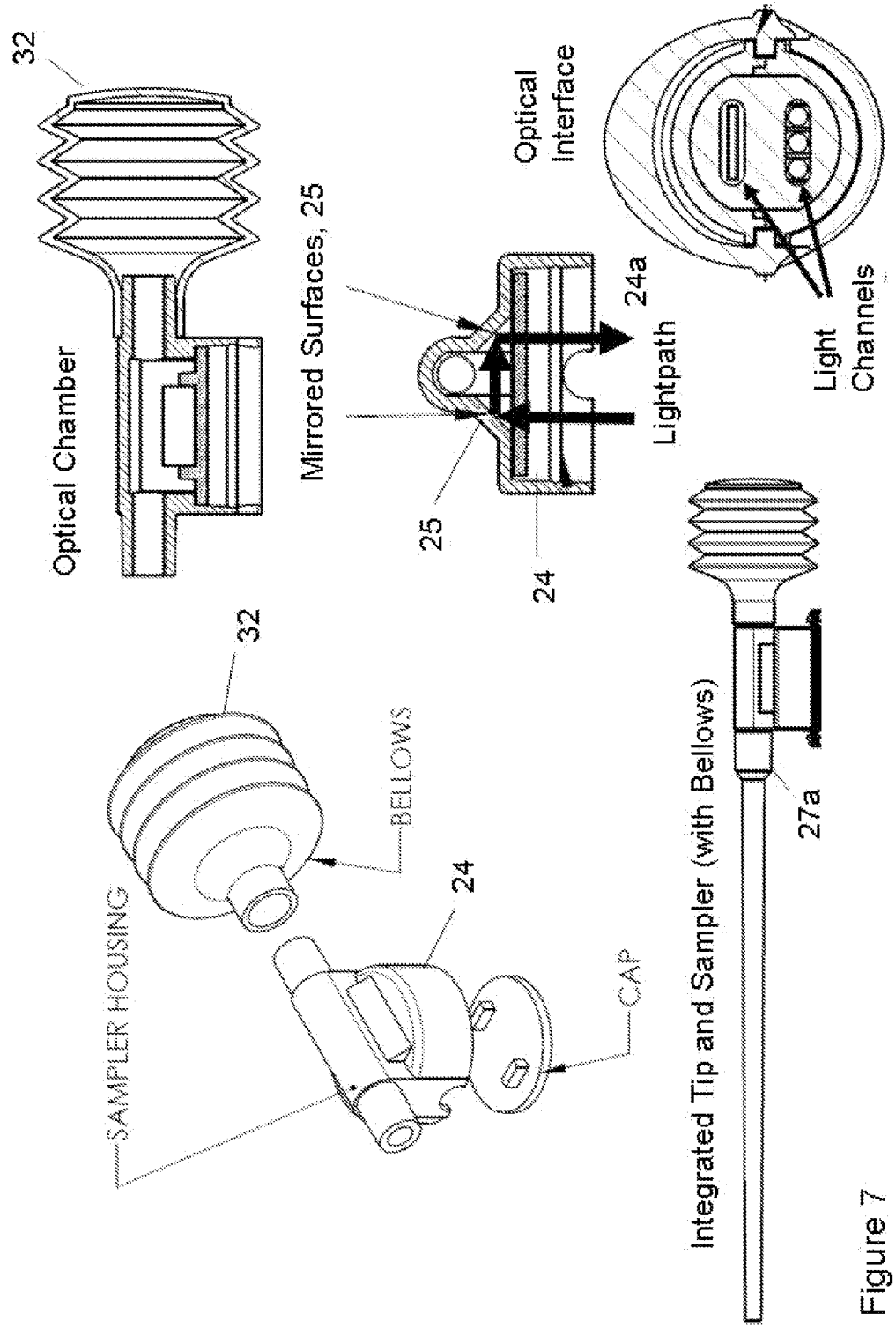
FIG. 7 illustrates an example embodiment of the spectral engine with the sampler and its sample chamber and bellows.
Figure 8:
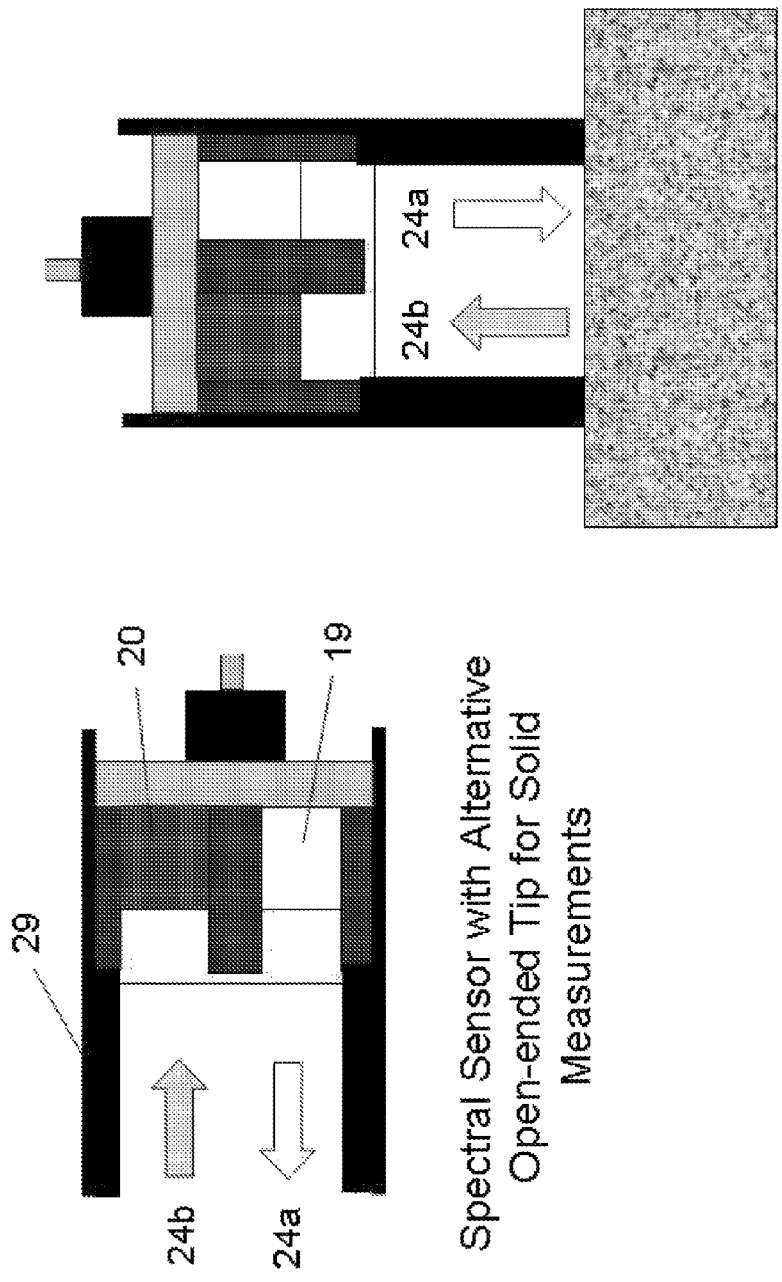
FIG. 8 illustrates example embodiments of the spectral engine alternatives for solid sampling.
Figure 9:
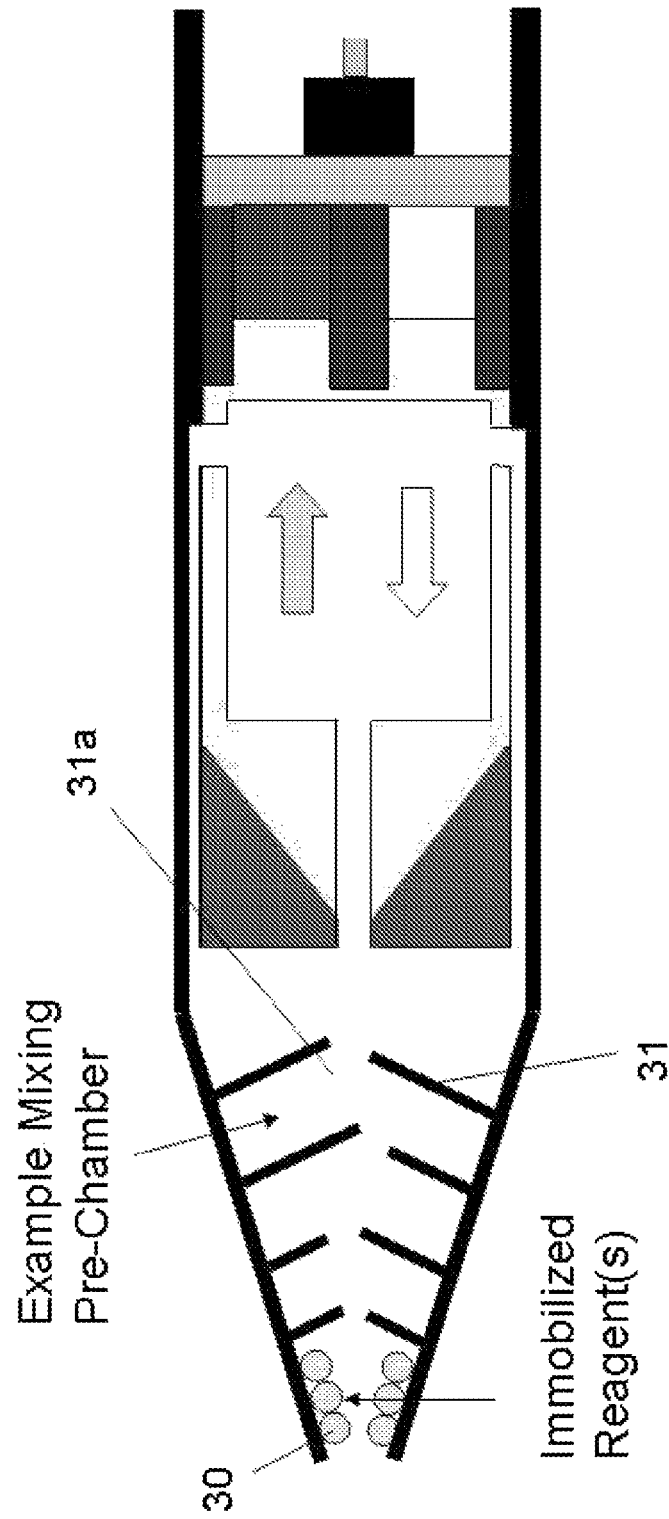
FIG. 9 illustrates an example embodiment of a Smart Tip™ located on the spectral engine.

The source and spectral detection components are interfaced to the sample measurement cavity (or chamber) via light pipes, light guides or light conduits. For the example illustrated, this is hard coupled to the sample chamber, and is designed to minimize optical crosstalk between the light source and the detection system. In alternative configurations, the light guides can be in the form of optical fibers. In visible and NIR spectral regions, optical pathlengths can range from 0.1 cm to 10 cm and these are considered to be optimum, dependent on the material to be measured. For visible measurements, the selection of pathlength is usually method dependent and is a function of the color density of the solutions under study. For the NIR, the longer pathlengths may be used for direct measurements made on organic chemicals, while shorter path lengths may be required for optically darker materials or water-based solutions. The pathlength is defined within the integrated construction of the sensor measurement cavity thereby providing close-coupled sample chamber 24 (FIGS. 5, 6 and 7). In order to make the sensor a single-sided entity, suitable for example for pipetting or dipping, it is necessary to use a folded path construction, as illustrated in FIGS. 5, 6 and 7. This folded pathlength 24a and 24b is obtained by the use of retro-reflective elements 25 located within the measurement cavity. Note that the example geometry is for a transmission-based measurement. Sample emission (such as fluorescence) or light scattering (such as turbidity) measurements can require alternative geometries, where the source and detection system are orthogonal (at 90 degrees) to each other, relative to the sample chamber. For most measurements the sample, as a liquid (FIGS. 6 and 7) or as a solid (FIG. 8) interacts directly with the source and detection system within the sample area. In the case of where a reagent is involved with a liquid sample, in the configurations shown in FIGS. 6 and 7, it is assumed that the reagent interacts with the liquid outside of the sample measurement area. However, an alternative is to feature an immobilized reagent, which is located within the light path. In such cases, the reagent may be included within a transparent substrate as pads 24c in the light path within the measurement cavity (FIG. 10) or on an opaque, reflective surface. In the latter case, the solid sampling approach of FIG. 8 is required for the measurement. Examples are pH or test-paper measurements, where the liquid sample reacts in situ with the reagent that is immobilized in a porous solid matrix, such as a sol gel or a membrane (organic or inorganic) or an absorbent paper matrix. In examples where immobilized reagents are used and the optical measurement is made within the light path, special tips or sample chambers will be used with the immobilized reagent. In the case of the special tips (FIG. 9) the immobilized reagent substrate is located within the fluid path of the tip. In the case of the implementation within the sample chamber the substrate including pads 24c is placed at the end of the entrance (and/or exit) points of the optical light guides.

Figure 11:
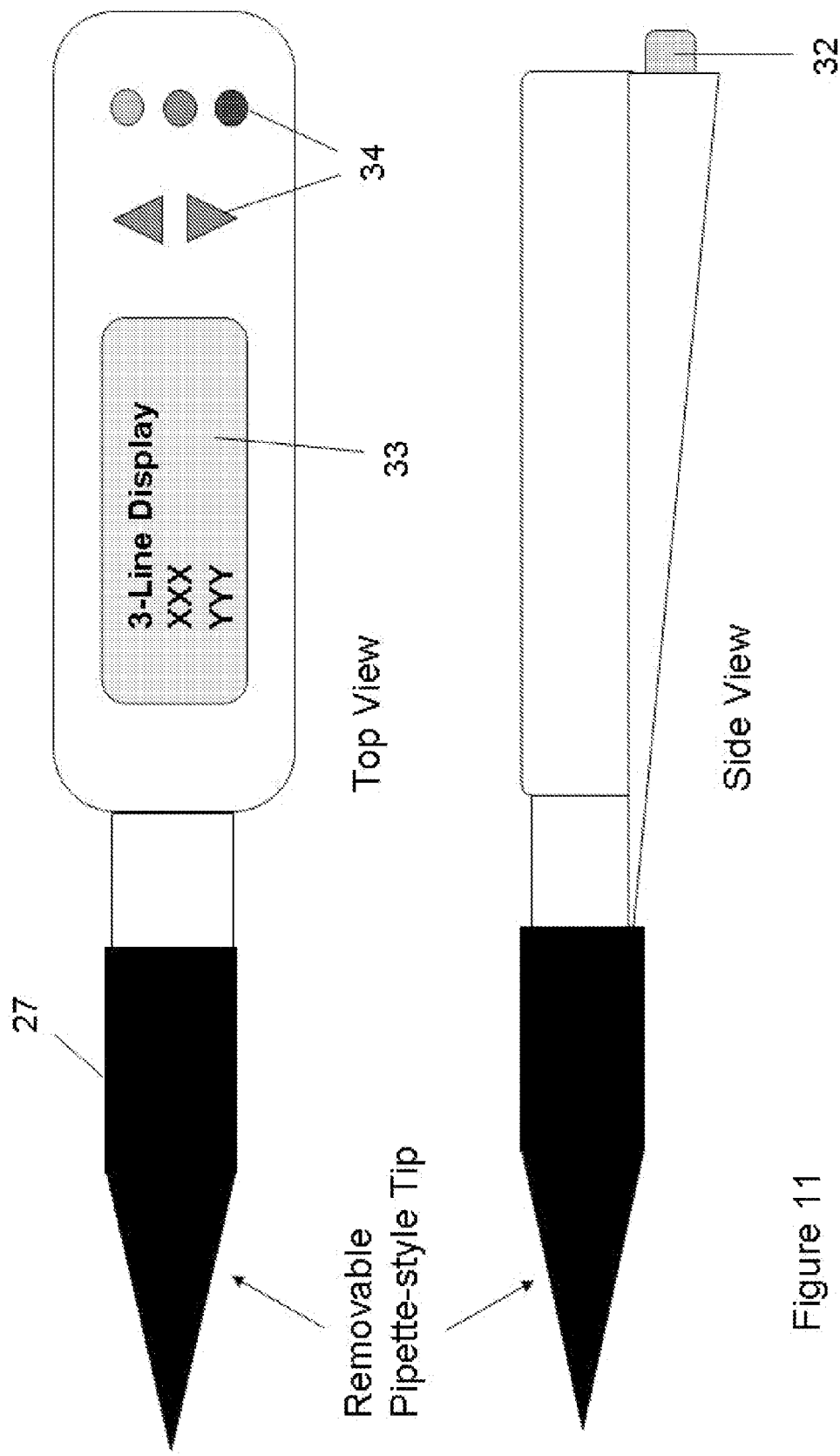
FIG. 11 illustrates an example embodiment for a pipette-style design for spectral sensor.
Figure 12:
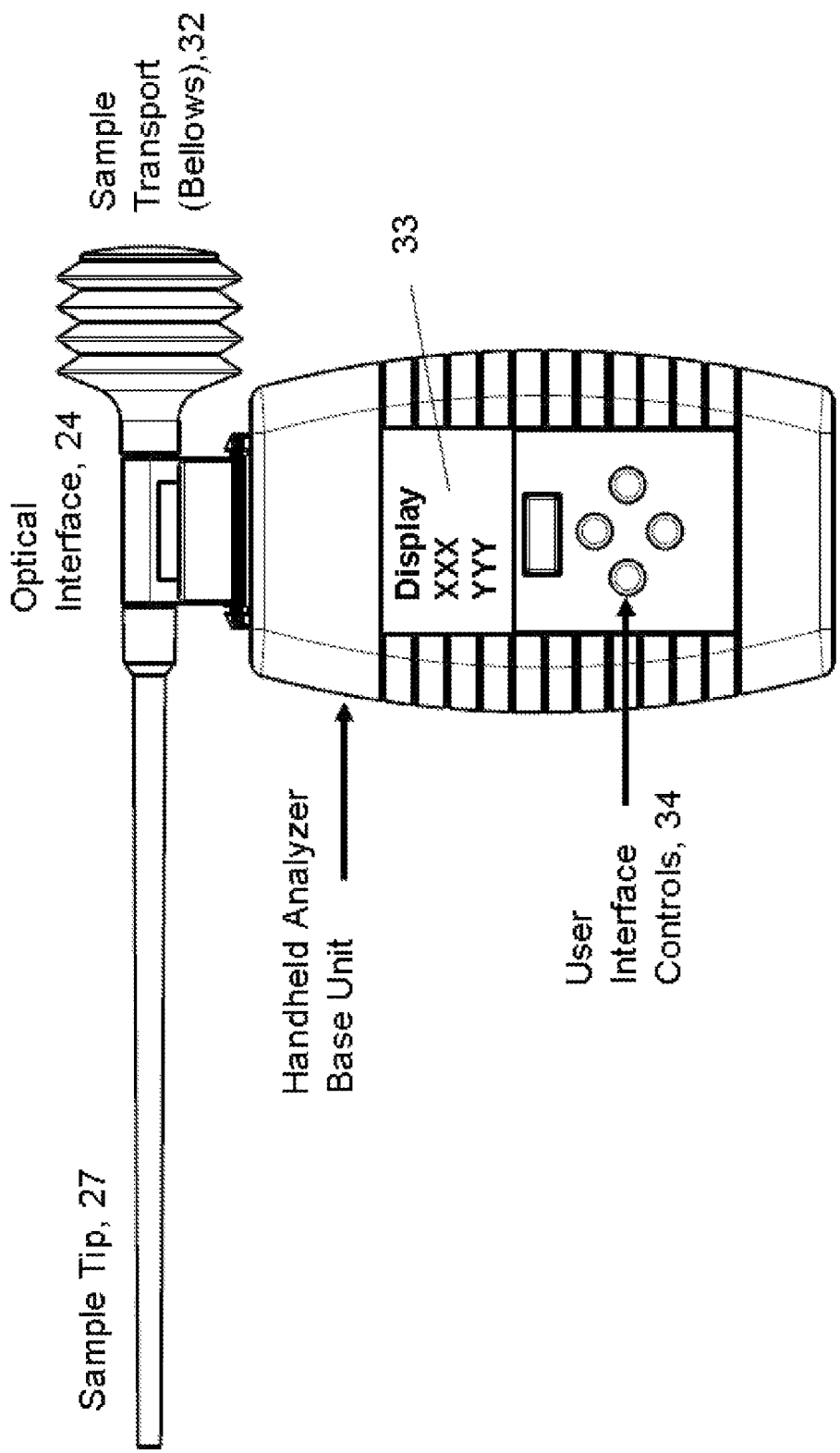
FIG. 12 illustrates an example embodiment for a handheld design for the spectral sensor.
Figure 13:
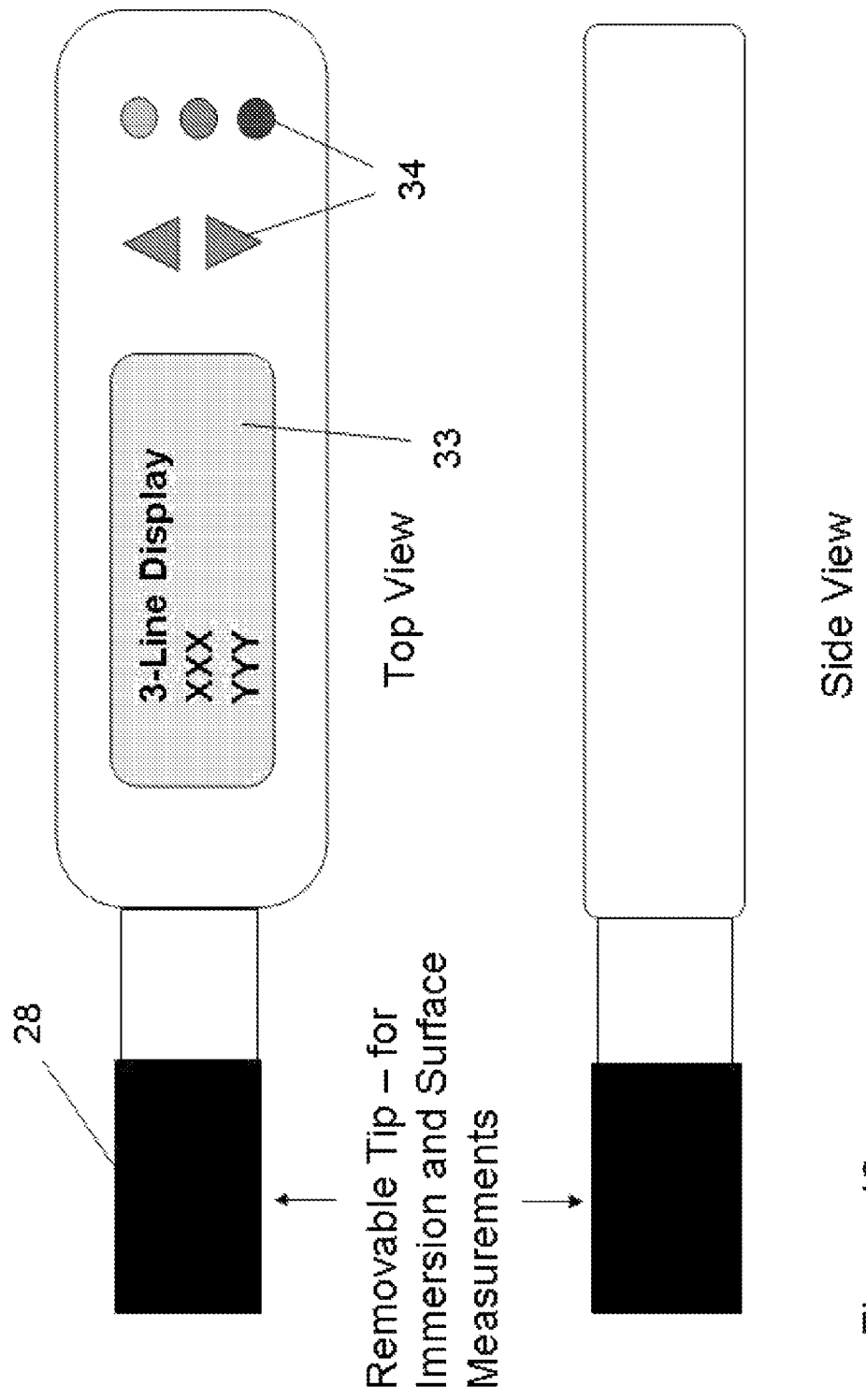
FIG. 13 illustrates an example embodiment of alternative design for an insertion spectral sensor.

In the example preferred embodiments shown in FIGS. 6, 7 and 8 the spectral engine is constructed as two separable parts. The spectral sensing components and associated electronics (FIG. 4) and the sample interface, which is intended to be removable, and optionally disposable. The spectral sensing components and the electronics are located within the main body of the sensor (FIGS. 11, 12 and 13). The sample chamber is located within the removable tip or sampler, which can be constructed in different forms dependent on the applications. In one version of the sensor, the device takes the form of a mechanical micro pipette where the sample is transported into the sensor tip via a built-in piston pump (or equivalent). In this form, the tip is constructed with the external appearance of a pipette tip 27 (FIG. 6 and FIG. 11). In a second version of the sensor, which is a preferred embodiment, the measurement module is independent of the sample transfer, which takes place within the completely separated sampler assembly. In this form the sampler has a common construction to a disposable pipette with a bellows (or bulb) style pumping (suction), and with the sample chamber mated on the side where the sample flow takes place. During the filling process the liquid fills the measurement cavity by the suction process, and any residual bubbles rise into the upper flow channel (or the bellows/bulb) and out of the optical path. The sensor can also be configured to measure liquids by immersion or insertion (a dip tip configuration). In this format, the sample enters the sampling area from slots, perforations or apertures in the sides of the tip 28 (FIG. 6 and FIG. 10). This form of sensor tip has a two part main construction, comprising an inner optically transparent part and an external optically opaque part. The construction of the outside part is such that there is no light leakage from the outside into the internal sample chamber or measurement area. Alternatively stated, the external part of the tip is constructed to eliminate the opportunity for external (ambient) stray light to enter the measurement zone. In the most common form of construction, both parts of the tip can be made from plastic materials (polymers). Also, in most cases, the materials can be fabricated from some form of co-extrusion process. Note that the internal reflective elements 25 for the sample chamber are to be fabricated from a reflective insert or with a reflective coating. In either case, the coating or the insert can be protected from the measurement medium by embedding within the plastic or by a protective top coat. In an alternative sampling configuration (FIG. 8), the sample tip 29 is designed to be open-ended. In this format, the spectral sensor is intended for use with solid materials, where the sensor measures the reflected light from the solid sample surface. This may be used to measure reacted test strips (pH strips, water testing strips, medical test strips, for example), color from solid surfaces (powders, extended solids and fabrics, for example), or material composition, such as a transparent coating.

The application of the standard tips or samplers for liquids is intended to serve either applications that involve the direct spectral measurement of liquid samples, based on their own natural color or natural absorption (UV or NIR for example) or fluorescence. In other examples, with the standard tips or samplers, the sensor will work as a spectrometer or photometer for a standard reagent-based measurement, where the reagent is mixed externally with the sample prior to sampling and measurement. Alternative forms of tip or sampler, known as a Smart Tip™, FIG. 9, or as a Smart Sampler™, FIG. 10 can both be included. The smart tip includes the reagent or reagents within the body of the tip. With the Smart Sampler, the reagent can be located within the tip and/or within the measurement chamber. For the smart tip the reagents are in an immobilized form 30, where they are either encapsulated within a water-soluble (or solvent-soluble) medium, or they are embedded within a water/solvent permeable membrane. In such cases, the reagent is mixed in situ as the sample is drawn into the entrance of the tip. The mixture of sample and reagent is then drawn through a series of vanes 31, that provide a "tortuous" pathway, or mixing pre-chamber 31a, where the two components (reagent(s) and sample) are thoroughly mixed and are given time to react. The mixed and reacted solution is then drawn into the measurement chamber. For most applications, this process is expected to be a smooth, single-step action, and is part of the overall sampling where the sample is drawn into the tip. In the case of the smart sampler, the reagent can be alternatively be immobilized within an adsorbent structure where mixing occurs by passage through the adsorbent material (FIG. 10, 30/31), or it can be immobilized in light transmitting pads 24c located within the light path of the measurement chamber (FIG. 10). The benefit of these approaches is that minimal reagent quantities are used, an ideal scenario for many modern applications in the bio-chemical and medical fields where specific reagents are extremely expensive. In addition, this approach eliminates any external contact with the reagents (important if the regent materials are toxic or intrinsically corrosive), and it simplifies disposal. The entire approach is environmentally friendly, eliminating the use of excess reagent materials and reducing the quantities of materials for disposal. The specific regents can be identified by the external design or appearance of the tip, by using color coding, bar coding or by the use of a technology such as RFID.

Three example embodiments of the sensor system are illustrated, FIGS. 11, 12 and 13. The first is the fully self-contained pipette-based version FIG. 11, is described as the SpectraPette™, which includes an integrated pumping system 32 for the sample transport. The pumping can be implemented in the form of a simple piston pump. Alternatively, a mechanized pumping, based on an electrical micro pump (rotary or piezo, for example) can be used. Note that this format can support either the standard measurement tips of the Smart Tips. A second format, where the sample is introduced via a sampler that contains the sample transport mechanism and is the form of a suction bulb or bellows, is illustrated in FIG. 12. In this format, the main body of the sensor is fully self-contained and only has a light path interface with the sampler. The complete measurement system, is designed to be hand-held, but is also designed to be freestanding on a solid surface. In the final example format, where the sample is introduced following emersion or insertion into the liquid, the sensor is a simpler construction because there is not the requirement for the pumping action for sample introduction (FIG. 13). All sensor formats are intended to be battery-powered, where standard dry cells or rechargeable batteries are used. The main body of the sensor includes a display 33 and push-button user interface controls 34 for the selection of methods, and the display of results, and a minimum set of controls. Note that the display is not limited to a three-line format, and can display graphical information as well as alpha-numerics. In the most basic form of the sensor, the controls 34 can include functions such as power on-off, method selection, measurement activation, and transmit (for the transmission of results/data). Automatic features can include auto-power down, and auto-transmit to a local central PC for data logging, of both raw and processed spectral data.

The approach offered is described as being based on a spectral engine (FIG. 1), which is further illustrated in its final embodiments in FIGS. 11, 12 and 13. The spectral engine includes the spectral sensing device (described above) 14 and 15, and the energy source 10 and 19, which can be either a broadband or narrowband source, dependent on the mode of measurement (broadband sources are used for NIR and visible absorption, narrowband sources are used for turbidity and fluorescence). White LEDs, LED arrays and tungsten bulbs are used as example broadband sources, and individual LEDs and semiconductor laser devices are used as narrowband sources. Another component of the spectral engine is the sample interface, which is typically a cavity or chamber 24. One of the key benefits offered by the system is that the sample chamber is optimized in size based on the physical dimensions of the spectral engine sample interface. The sizes of the detection devices are, for example, 1 mm×8 mm 15 and approximately 3 mm×3 mm (matrix sensor 16). Scaling the sample cell to these physical dimensions can produce sample chamber volumes as low as 80 microliters. The advantage gained here is that a minimum sample size is required, which effectively eliminates any sample temperature effects, and significantly reduces the amount of reagents that have to be dispensed for reagent-based applications. The volume requirement for reagents can be reduced down by as much as 1000 times, which reduces reagent consumption and operating costs. The final critical set of components of the spectral engine is the electronics. An example of the functional electronics is provided in FIG. 3, which are physically located within the total sensor body as illustrated in FIGS. 5 to 8 as 22. Up to two microprocessors, and possibly more can be used for the initial data handling (processor #1 17, and then the data massaging processor #2 18). The final processor 18 can feature onboard memory to store methods, calibrations and results, and can handle communications to displays (if required), external devices via serial connections and also wireless communications if the option is used. A single advanced processor is a practical alternative to the two processor format.

The spectral sensor implementation is based on basic two-part construction featuring the main spectral sensing system, with common display and controls, and a disposable component; a tip FIGS. 11 and 13, or a sampler FIG. 12. Two main formats are offered; one with sample transport, in the format of a micro-pipette (FIG. 11) or a disposable pipette (FIG. 12), and the other as a dip (insertion) or surface measurement device (FIG. 13). The function of the sensor is defined in terms of the tip or sampler (27, 28 or 29), and the method of measurement selected from the integrated display 33.

The fundamental aspects of the present invention lead not only to increased productivity, but ready implementation as a portable system for at least the four target application areas: water, chemical, and petroleum, food and beverages, and clinical and medical. In the case of water, an apparatus in accordance with the invention expands testing out of the laboratory, and enables field-based water and environmental testing. It provides similar advantages in a number of consumer-oriented markets, including home-based water testing (including swimming pools), food safety testing, and home-based medical testing.

While the present invention has been described with particular reference to certain specifically described components and methods, it is to be understood that it includes all reasonable equivalents thereof, including those as defined by the attached claims.

I claim:

1. An integrated sensing module, said sensing module comprising:
    an optical filter assembly and a light or energy sensitive array, the optical filter assembly and the light or energy sensitive array forming a solid-state device either matched directly in spectral response to a source, or capable of responding to wavelengths over a broad spectral range from one or more sources, the optical filter assembly and the light or energy sensitive array being aligned for direct coupling to one another thereby forming interfacing optics and preserving spectral resolution of the optical filter assembly;
    system optics;
    one or more on-board processors; and
    a memory for storing reference spectral data recorded in the absence of analyte material, the reference spectral data being used to provide a ratio of energy detected by a sample measurement and energy obtained from the reference spectral data, thereby providing a direct measure of the energy absorbed by the sample and system optics.

2. An integrated sensing module, said sensing module comprising:
    an optical filter assembly and a light or energy sensitive array, the optical filter assembly and the light or energy sensitive array forming a solid-state device either matched directly in spectral response to a source, or capable of responding to wavelengths over a broad spectral range from one or more sources, the optical filter assembly and the light or energy sensitive array being aligned for direct coupling to one another thereby forming interfacing optics and preserving spectral resolution of the optical filter assembly;
    a memory for storing reference spectral data; and
wherein the reference spectral data recorded represents optical interaction of multiple analytes, thereby enabling more than one analysis to be performed, or where a more complex analysis is performed in the event that a condition being monitored provides different independent responses at different wavelengths, the sensing module providing an output for either multiple components or measurement of a complex condition by use of modeling techniques.

3. An integrated sensing module, said sensing module comprising:
   an optical filter assembly and a light or energy sensitive array, the optical filter assembly and the light or energy sensitive array forming a solid-state device either matched directly in spectral response to a source, or capable of responding to wavelengths over a broad spectral range from one or more sources, the optical filter assembly and the light or energy sensitive array being aligned for direct coupling to one another thereby forming interfacing optics and preserving spectral resolution of the optical filter assembly;
   a processor for processing the signal produced from the light or energy sensitive array; and
   an on-board memory for storing calibration coefficient data for simple and complex calibrations, including simple linear response calibrations, second order and higher response calibrations, multivariate models for complex calibrations and/or multicomponent analyses, and storage of methods linked to said calibration coefficient data.

4. An integrated sensing module, said sensing module comprising:
   an optical filter assembly and a light or energy sensitive array, the optical filter assembly and the light or energy sensitive array forming a solid-state device either matched directly in spectral response to a source, or capable of responding to wavelengths over a broad spectral range from one or more sources, the optical filter assembly and the light or energy sensitive array being aligned for direct coupling to one another thereby forming interfacing optics and preserving spectral resolution of the optical filter assembly;
   a processor for processing the signal produced by the light or energy sensitive array; and
   an on-board memory for storing multiple spectra, multiple calibrations, and multiple methods using said calibrations.

5. An integrated sensing module, said sensing module comprising:
   an optical filter assembly and a light or energy sensitive array, the optical filter assembly and the light or energy sensitive array forming a solid-state device either matched directly in spectral response to a source, or capable of responding to wavelengths over a broad spectral range from one or more sources, the optical filter assembly and the light or energy sensitive array being aligned for direct coupling to one another thereby forming interfacing optics and preserving spectral resolution of the optical filter assembly;
   a processor for processing the signal produced by the light or energy sensitive array; and
   an on-board memory for storing pre-loaded or downloaded calibration coefficients for defined methods, the methods being fully defined to include data acquisition parameters, data pre- and post processing, numerical calculations and data transfer and/or display.

6. The sensing module of claim 5, wherein downloading is carried out directly via a built-in serial interface, or over an optional wireless communications interface.

7. An integrated sensing module, said sensing module comprising:
   an optical filter assembly and a light or energy sensitive array, the optical filter assembly and the light or energy sensitive array forming a solid-state device either matched directly in spectral response to a source, or capable of responding to wavelengths over a broad spectral range from one or more sources, the optical filter assembly and the light or energy sensitive array being aligned for direct coupling to one another thereby forming interfacing optics and preserving spectral resolution of the optical filter assembly; and
   a processor having at least one of:
      a computation means for performing computations including concentration calculations;
      means for processing of intelligent sensor outputs;
      support for standard data formats, standard protocols and standard forms of communications, including serial and bus-oriented communications formats; and
      support of hardware based and wireless based communications protocols.

8. An integrated sensing module, said sensing module comprising:
   an optical filter assembly and a light or energy sensitive array, the optical filter assembly and the light or energy sensitive array forming a solid-state device either matched directly in spectral response to a source, or capable of responding to wavelengths over a broad spectral range from one or more sources, the optical filter assembly and the light or energy sensitive array being aligned for direct coupling to one another thereby forming interfacing optics and preserving spectral resolution of the optical filter assembly;
   the sensing module being formed in combination with and integrated into a fully self-contained handheld device configured to operate with disposable components selected based on application and method required for measurement; and
   wherein the disposable components are in the form of tips and/or samplers, where specific reagents are integrated into each body of the tips or within each measurement cavity of the samplers.

9. An integrated sensing module, said sensing module comprising:
   an optical filter assembly and a photodiode, the optical filter assembly and the photodiode forming a solid-state device either matched directly in spectral response to a source, or capable of responding to wavelengths over a broad spectral range from one or more sources, the optical filter assembly and the photodiode being aligned for direct coupling to one another thereby forming interfacing optics and preserving spectral resolution of the optical filter assembly; and the sensing module being formed in combination with and integrated into a fully self-contained handheld device configured as a surface measurement device with an open-ended sample tip.

10. The sensing module of claim 9, wherein the optical filter assembly is a continuous linear variable filter.

11. The sensing module of claim 9, wherein the optical filter assembly is a filter array.

12. The sensing module of claim 11, wherein the filter array is a patterned filter.

13. The sensing module of claim 11, wherein the filter array is a mosaic filter.

14. The handheld device of claim 9, wherein the surface measurement device is configured for reflectance and/or transflectance measurements from a surface.

15. The handheld device of claim 14, wherein the surface measurement device is further configured for measurement of bio-materials in medical applications.

16. An integrated sensing module, said sensing module comprising:
    an optical filter assembly and a complementary metal-oxide semiconductor (CMOS) array detector package, said optical filter assembly and said CMOS array detector package forming a solid-state device either matched directly in spectral response to a source, or capable of responding to wavelengths over a broad spectral range from one or more sources, said optical filter assembly and said CMOS array detector package being aligned for direct coupling to one another thereby forming interfacing optics and preserving spectral resolution of the optical filter assembly; and the sensing module being formed in combination with and integrated into a fully self-contained handheld device configured as a surface measurement device with an open-ended sample tip.

17. The sensing module of claim 16, wherein the optical filter assembly is a continuous linear variable filter.

18. The sensing module of claim 16, wherein the optical filter assembly is a filter array.

19. The sensing module of claim 18, wherein the filter array is a patterned filter.

20. The sensing module of claim 18, wherein the filter array is a mosaic filter.

21. The handheld device of claim 16, wherein the surface measurement device is configured for reflectance and/or transflectance measurements from a surface.

22. The handheld device of claim 21, wherein the surface measurement device is further configured for measurement of bio-materials in medical applications.

\* \* \* \* \*